United States Patent
Yang

(10) Patent No.: US 11,111,479 B2
(45) Date of Patent: Sep. 7, 2021

(54) METHODS AND KITS FOR GUIDED STEM CELL DIFFERENTIATION

(71) Applicant: Shengyuan Yang, West Melbourne, FL (US)

(72) Inventor: Shengyuan Yang, West Melbourne, FL (US)

( * ) Notice: Subject to any disclaimer, the term of this patent is extended or adjusted under 35 U.S.C. 154(b) by 124 days.

(21) Appl. No.: 15/652,938

(22) Filed: Jul. 18, 2017

(65) Prior Publication Data

US 2019/0024052 A1 Jan. 24, 2019

(51) Int. Cl.
*C12N 5/077* (2010.01)
*C12N 5/0775* (2010.01)

(52) U.S. Cl.
CPC ......... *C12N 5/0653* (2013.01); *C12N 5/0654* (2013.01); *C12N 5/0663* (2013.01); *C12N 2506/1384* (2013.01); *C12N 2513/00* (2013.01); *C12N 2531/00* (2013.01); *C12N 2533/12* (2013.01); *C12N 2535/00* (2013.01)

(58) Field of Classification Search
CPC ............ C12N 2513/00; C12N 2535/00; C12N 5/0662; C12N 5/0654
See application file for complete search history.

(56) References Cited

U.S. PATENT DOCUMENTS

| | | | |
|---|---|---|---|
| 719,591 | A | 2/1903 | Heinrich |
| 8,802,430 | B2 | 8/2014 | Yang |
| 9,021,897 | B2 | 5/2015 | Yang |
| 2008/0057578 | A1 | 3/2008 | Kuwabara |
| 2009/0197333 | A1 | 8/2009 | Saito et al. |
| 2010/0129908 | A1 | 3/2010 | Fang |
| 2010/0151491 | A1 | 6/2010 | Himmelhaus et al. |
| 2010/0330644 | A1 | 12/2010 | Feinberg et al. |
| 2013/0252337 | A1 | 9/2013 | Yang |
| 2015/0072430 | A1 | 3/2015 | Yang |

OTHER PUBLICATIONS

Kodali et al. "Cell-Microsphere Constructs Formed with Human Adipose-Derived Stem Cells and Gelatin Microspheres Promtes Stemness, Differentiation, and Controlled Pro-Angiogenic Potential", (2014), Macromolecular Bioscience, vol. 14: 1458-1468. (Year: 2014).*

Werner et al. "Surface Curvature Differentially Regulates Stem Cell Migration and Differentiation via Altered Attachment Morphology and Nuclear Deformation" published online Dec. 20, 2016, Advanced Science, vol. 4, issue 2, No. 1600347: 1-11. (Year: 2017).*

Damlijanovic, et al, Bulk and Mircropatterned Conjugation of Extracellular Matrix Proteins to Characterized Polyacrylamide Substrates for Cell Mechanotransduction Assays:, Bio Techniques, vol. 39, No. 6 pp. 847-851.

Engler, et al, "Surface Probe Measurements of the Elasticity of Sectioned Tissue, Thin Gels and Polyelectrolyte Multilayer Films: Correlations Between Substrate Stiffness and Cell Adhesion", Surface Science 570, p. 142-159.

Hwang et al., Controlled cellular orientation on PLGA microfibers with defined diameters, Biomed Microdevices (2009) 11:739-746.

James et al., Subcellular Curvature at the Perimeter of Micropatterned Cells Influences Lamellipodial Distribution and Cell Polarity, Cell Motility and the Cytoskeleton 65: 841-852 (2008).

Kang et al., Porous Poly(Lactic-Co-Glycolic Acid) Microsphere as Cell Culture Substrate and Cell Transplantation Vehicle for Adipose Tissue Engineering, Tissue Engineering: Part C vol. 14, No. 1, 2008.

Rumpler et al., The effect of geometry on three-dimensional tissue growth, J. R. Soc. Interface (2008) 5, pp. 1173-1180.

Smeal et al., Substrate Curvature Influences the Direction of Nerve Outgrowth, Annals of Biomedical Engineering, vol. 33, No. 3, Mar. 2005, pp. 376-382.

Wang, et al, "Preparation of a Flexible, Porous Polyacrylamide Substrate for Mechanical Studies of Cultured Cells", Methods in Enzymology, vol. 298, p. 489-496, 1998.

Yang, et al. Micromachined Force Sensors for the Study of Cell Mechanics, American Institute of Physics, Review of Scientific Instruments, p. 044307-044307.8. 2005.

* cited by examiner

*Primary Examiner* — Teresa E Knight

(57) ABSTRACT

The present disclosure provides methods, and related kits, for directing cell attachment and spreading on a substrate and inducing isotropic spreading of cells; provides methods, and related kits, for cell sorting; and further provides methods, and related kits, for guided induction of stem cell differentiation.

3 Claims, 15 Drawing Sheets

METHODS AND KITS FOR GUIDED STEM CELL DIFFERENTIATION

GOVERNMENT SUPPORT

The subject invention was made with government support under a research project supported by the National Science Foundation (NSF) CAREER program grant number 0845954. The government has certain rights in the invention.

CROSS-REFERENCE TO RELATED APPLICATIONS

This application is related to co-pending U.S. patent application Ser. No. 15/652,928 filed Jul. 18, 2017, entitled, "Methods and kits for cell sorting," and U.S. patent application Ser. No. 15/652,921, filed Jul. 18, 2017, entitled, "Methods and kits for directing cell attachment and spreading," both of which are incorporated herein by reference in their entireties.

BACKGROUND

The interactions between cells and their surrounding environments have been receiving increased attention over the past twenty years. Cell-substrate interactions can profoundly affect cell behavior, including adhesion, spreading, migration, division, differentiation, apoptosis, and internal cellular signaling. The binding interactions between cells and their material layer(s) are influenced by mechanical stimuli, such as material stiffness and material curvatures. The effects of material stiffness on cell behaviors have been extensively studied (Alenghat and Ingber, 2002; Wang et al., 2002; Janmey and Weitz, 2004; Yeung et al., 2004; Engler et al., 2004; Chen et al., 2004; Wong et al., 2004; Brown et al., 2006; Engler et al., 2006; Kasza et al., 2007; Rodriguez et al., 2013); however, the cellular responses to the geometry of a substrate, e.g., the curvature of the substrate, are not well-documented (Chen et al., 1997; Sniadecki et al., 2006; Sanz-Herrera et al., 2009; Digabel et al., 2010; Baker and Chen, 2012). Since the materials on which the cells grow in vivo are normally not flat, the responses of cells to material curvatures should also be a fundamental aspect of cell mechanosensitivity and mechanotransduction. The importance of material curvature effects on cell behaviors can be illustrated by understanding the process of cell attachment and growth on curved surfaces of bones and implants in vivo.

Normal cell natural spreading is random in every direction, and the resulting cell spread shape is irregular and non-uniform (Alberts et al., 2015). Two-dimensional (2D) geometric patterns and chemical patterns have been widely generated by microfabrication technologies to define the spread shapes of living cells in in vitro cultures, which has opened many opportunities for and re-shaped the area of cellular bioengineering and mechanobiology (Kilian et al, 2010; Wan et al., 2010; Tang et al., 2012; Tao et al., 2013). Cell isotropic-spreading, where the resulting cell outline or boundary is roughly circular and smooth which means the extent of the cell spreading in every direction is roughly the same from the geometric center of the cell, has been realized by culturing the cells in geometrically-patterned and chemically-patterned circular areas (Chen et al., 1997; Liu and Chen, 2007; Song et al., 2011), but the geometric patterning and or the chemical patterning must be there to control or restrict the spreading of a cell to realize the cell isotropic-spreading, which means the realized cell isotropic-spreading is not a cell natural spreading. Therefore, it is difficult to take advantage of or use cell isotropic-spreading realized by culturing cells in geometrically-patterned and chemically-patterned circular areas for studies and applications in cellular bioengineering and mechano-biology.

Further, in response to geometrical stimuli cells change their morphologies and motilities, and these changes are most likely caused by the changes in the intracellular forces associated with the changes in the cell focal adhesions and actin stress fibers due to the geometrical stimuli (Folch and Toner, 2000; Discher et al., 2005; Georges and Janmey, 2005; Vogel and Sheetz, 2006; Vartanian et al., 2008; Cheng et al., 2009; Wan et al., 2010; Rape et al., 2011; Song et al., 2011; Yao et al., 2013; Meehan and Nain, 2014). The geometry of a substrate also determines the orientation and rate of cell growth (Smeal et al., 2005; Rumpler et al., 2008; Hwang et al., 2009; Veiseh et al., 2015; Viswanathan et al., 2015; Zadpoor, 2015).

BRIEF SUMMARY

Since the surface curvature of a substrate is a major descriptive parameter of the geometry of the substrate, studies on the cellular responses to the surface curvature of a substrate are necessary for understanding the cellular behaviors in three-dimensional (3-D) micromechanical environments and for designing effective and efficient 3-D micromechanical environments to control cell and tissue developments. It is difficult to take advantage of or use cell isotropic-spreading realized by culturing cells in geometrically-patterned and chemically-patterned circular areas for studies and applications in cellular bioengineering and mechanobiology. Methods to control spreading of a cell on a non-flat substrate are needed, especially, for 3-D bioengineering and mechanobiology.

The present disclosure provides methods, and related kits, for directing cell attachment and spreading on a substrate and inducing isotropic spreading of cells. The disclosure also provides methods, and related kits, for cell sorting; and further provides methods, and related kits, for guided induction of stem cell differentiation.

In one aspect, the disclosure provides methods of cell sorting, comprising culturing a mixed population of cell types, the mixed population comprising a target cell and a non-target cell, on a curved substrate in the presence of cell culture media for a time sufficient for one of a target or a non-target cell to attach to the substrate; and removing, or separating, the cell culture media from the curved substrate, wherein the target cell is contained either in the cell culture media or on the curved substrate, wherein the non-target cell is contained in the cell culture media if the target cell is contained on the curved substrate or the non-target cell is contained on the curved substrate if the target cell is contained in the cell culture media. In a further aspect, the disclosure provides kits for cell sorting, comprising a first reagent, wherein the first reagent comprises a curved substrate. In yet another aspect, the disclosure provides kits for cell sorting, comprising a first reagent, wherein the first reagent comprises a spherical substrate having a diameter less than about 500 μm.

In another aspect, the present disclosure provides methods for directing cell attachment and spreading on a substrate, comprising culturing a cell on a curved substrate in the presence of cell culture media, wherein attachment and spreading increases as the curvature of the substrate decreases. In a further aspect, the disclosure provides kits for directing cell attachment and spreading on a substrate, comprising a first reagent, wherein the first reagent comprises a curved substrate.

In another aspect, the disclosure provides methods for guided induction of stem cell differentiation, comprising culturing a stem cell on a curved substrate in the presence of cell culture media. In a further aspect, the disclosure provides kits for guided induction of stem cell differentiation, comprising a first reagent, wherein the first reagent comprises a curved substrate.

In one aspect, the present disclosure provides methods of culturing cells on micro ball embedded polyacrylamide (PA) gels (non-flat and 3-D) such that the cells isotropically spread over the balls and the adjacent gel surfaces. In another aspect, the disclosure provides methods of inducing isotropic spreading of cells, comprising culturing a cell on a curved substrate, the curved substrate partially embedded in a gel surface, wherein the cell isotropically spreads over the curved substrate and onto the gel surface. In a further aspect, the disclosure provides kits for inducing isotropic spreading of cells, comprising a first reagent, wherein the first reagent comprises a curved substrate.

In some embodiments, the curved substrate comprises an array of curved substrates.

The methods, and related kits, herein described can be used in connection with pharmaceutical, medical, and veterinary applications, as well as fundamental scientific research and methodologies, as would be identifiable by a skilled person upon reading of the present disclosure. These and other objects, features and advantages of the present disclosure will become clearer when the drawings, as well as the detailed description, are taken into consideration.

BRIEF DESCRIPTION OF THE DRAWINGS

For a fuller understanding of the nature of the present disclosure, reference should be had to the following detailed description taken in connection with the accompanying figures.

DETAILED DESCRIPTION OF THE DISCLOSURE

Figure 1:
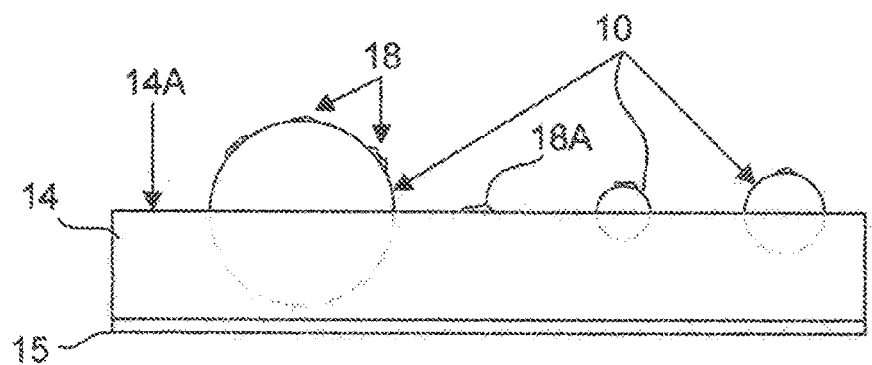
FIGS. 1, 2, 3 and 4 illustrate various embodiments of microstructures embedded in various material layers.

Several aspects of the disclosure are described below, with reference to examples for illustrative purposes only. It should be understood that numerous specific details, relationships, and methods are set forth to provide a full understanding of the disclosure. One having ordinary skill in the relevant art, however, will readily recognize that the disclosure can be practiced without one or more of the specific details or practiced with other methods, protocols, reagents, cell lines, and animals. The present disclosure is not limited by the illustrated ordering of acts or events, as some acts may occur in different orders and/or concurrently with other acts or events. Furthermore, not all illustrated acts, steps, or events are required to implement a methodology in accordance with the present disclosure. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the disclosure. As used herein, the articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

The term "surface curvature of a substrate" is used interchangeably with the term "substrate curvature."

In one aspect, the present disclosure provides methods of directing cell attachment and spreading on a substrate, comprising culturing a cell on a curved substrate in the presence of cell culture media, wherein attachment and spreading increases as the curvature of the substrate decreases. In a related aspect, the present disclosure provides a polyacrylamide (PA) gel embedded with curved substrates of various diameters to study cell mechanobiological responses to curvatures, patterns of various curvatures and other surface interface parameters. In yet another aspect, the disclosure provides methods of inducing isotropic spreading of cells, comprising culturing a cell on a curved substrate, the curved substrate partially embedded in a gel surface, wherein the cell isotropically spreads over the curved substrate and onto the gel surface.

In the various described embodiments, the curved substrates for use in the methods and kits described herein can range in size from about 1 nanometer to about 10 millimeters. In one application, NIH-3T3 mouse fibroblasts were cultured on glass balls having diameters ranging from about 5 micrometers to about 2 millimeters, and the cell morphologies analyzed by using an optical microscope and a 3D confocal laser scanning microscope. It was found that the fibroblasts are sensitive to the curvatures of the balls, and there are significant differences in the attachment rates, migration speeds, and morphologies for cells cultured on glass balls of diameters at or below about 500 micrometers.

Figure 5:
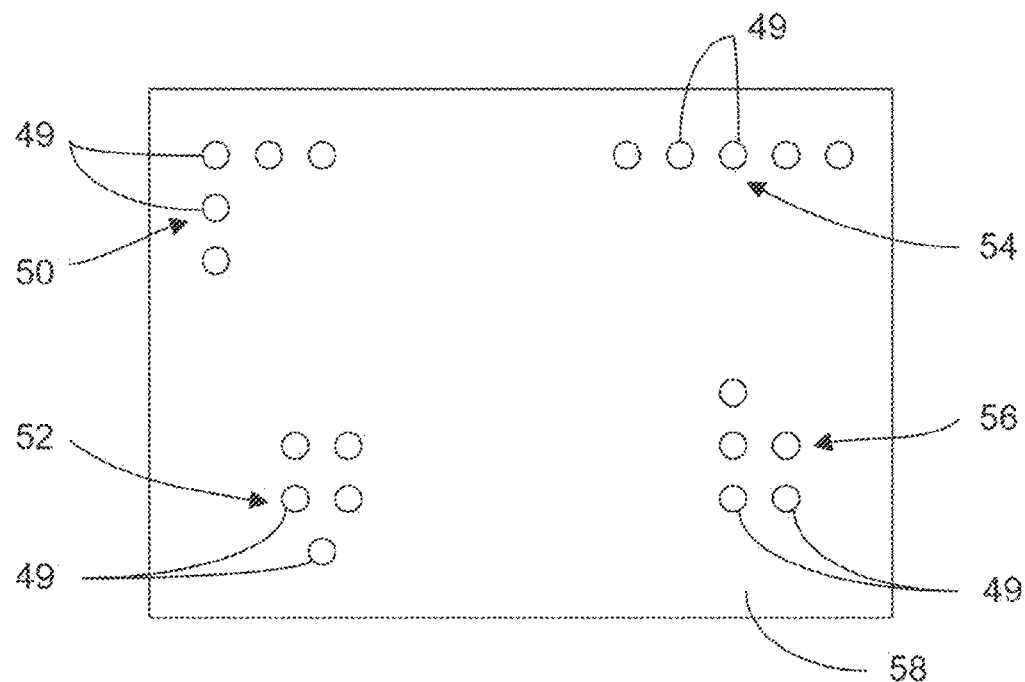
FIG. 5 illustrates an array of various clusters of microstructures.

The curved substrates for use in the various described methods and kits herein, whether all having the same shape or different shapes and whether all having the same size or different sizes, will share the characteristic that they will have a curvature. The substrates can be disposed within a gel or another material layer, to provide various shapes, shape patterns, curvatures, and curvature patterns for cell and tissue culturing and for use in other surface and interface applications. In some embodiments, the curved substrate comprises an array or arrays of curved substrates, where in an array of curved substrates, the shape and curvature and the material of each substrate can be same or can be different, and the pattern of the array can be well-defined or can be random, and the patterns of two arrays can be same or can be different, and the arrangement or distribution of arrays can be well-defined or can be random. The shapes can be predetermined by an ordered placement (e.g., uniform, periodic or symmetrical) of the curved substrates or the curved substrates can be randomly distributed within the gel or another material layer to provide random shapes and patterns. Both the ordered and random placement of the curved substrates within the gel or another material layer are important for use in cell and tissue culturing and in other surface and interface applications. Curved substrates 49, see FIG. 5, can be disposed in a single pattern within the gel or another material layer or can be disposed in clusters of several different patterns 50, 52, 54, and 56 across the surface of a gel 58 as shown in FIG. 5. In lieu of patterned arrangements, the curved substrates 49 can be placed randomly within the surface of the gel 58.

The curved substrates 49 for use in the various described methods and kits herein can exhibit any of the following shapes: ball-like, spherical, elliptical, oval, convex, concave, and combinations thereof. In some embodiments, the curved substrate is a spherical substrate, as shown in FIG. 5, such as, e.g., a ball. Any other defined or random shapes having any curvature can also be utilized. The substrates can also be solid or hollow, such as a spherical shell. In certain embodiments, the curved substrates comprise glass balls. The curves or shape of the substrates can be controlled to provide any predetermined curvature or, alternatively, the substrates can be formed to exhibit random curves and/or random shapes. In some embodiments, the curved substrates have been illustrated and described as concave (i.e., having a negative curvature) in shape. This is not necessarily required, as convex (i.e., having a positive curvature) substrate shapes are also useful in the methods and kits described herein. Substrate shapes useful in embodiments of the present disclosure are described in U.S. Pat. Nos. 8,802, 430 and 9,512,397, which are incorporated herein by reference.

In certain embodiments, the curved substrates have defined curvature. In certain embodiments, these values may be random, while in other embodiments, the values are not random but instead are defined based on the application. Whether random or defined, the substrates are fabricated according to these parameters and then loaded into or onto a material layer, or alternatively provided in a liquid suspension (e.g., cell culture media or buffer media) for use in cell or tissue culturing and in other surface and interface applications as described herein.

The curved substrate may also comprise a coating layer selected from the group consisting of a cell adhesive, a cell adhesion-promotor, a cell repellent, or a combination thereof. The entire or part of the surface of the curved substrate can be coated or functionalized by a layer of cell adhesives or cell adhesion-promotors, such as but not limited to, extracellular matrix proteins, fibronectin, collagen, laminin, etc. or a layer of cell repellents such as but not limited to, polyethylene glycol (PEG), etc., to promote or to inhibit the adhesion of the target or non-target cell onto the curved substrate.

In specific embodiments, the curved substrate is a spherical substrate, wherein the attachment and spreading of cells increases as the diameter of the spherical substrate increases. For example, when the spherical substrate comprises a diameter of between about 500 µm and about 6 mm, the attachment and spreading may be influenced in that both attachment and spreading increases as the diameter of the spherical substrate increases from about 500 µm to about 6 mm. Particularly useful for inducing isotropic spreading of cells, the spherical substrate may have a diameter of between about 5 µm and about 100 µm.

The curved substrates may be made of plastic, polydimethylsiloxane (PDMS), glass, silicon, or silicon nitride or any other material suitable for use in cell and tissue culturing or in any other surface interface applications. Materials that will permit the culturing of cells thereon, i.e., the material should preferably exhibit a curvature (convex or concave, or be able to change its shape in situ) and be able to retain that curvature during cell/tissue culturing can also be used. Also, all the curved substrates utilized in any one cell culturing experiment do not need to comprise the same material or the same shape.

FIGS. 1-4 illustrate substrate configurations and arrangements that are useful in the methods and kits disclosed. FIG. 1 illustrates curved substrates 10 embedded in a PA gel platform 14 for use in cell and tissue culturing and in other surface and interface applications in the methods and kits described herein. The PA gel platform is disposed on a material layer 15. In this platform, some cells 18 reside on the top of the curved substrates 10 while other cells 18A live on a surface 14A of the PA gel platform 14.

The extent to which the curved substrates are embedded in the gel can be randomly determined, for example, by simply dropping the curved substrate onto an exposed surface of the gel. In another embodiment, the curved substrates can be disposed such that an equal volume of each substrate extends above the gel surface 14A or each substrate extends an equal distance above the gel surface 14A.

The gel platform 14 functions as both a soft material layer and an adhesive surface to prevent any sliding or rolling of the glass balls 10. As can be seen in a scanning electron microscope (SEM) image of this platform (not shown), glass balls of 900 micrometers diameter, 500 micrometers diameter, and below 300 micrometers diameters extend out from an upper surface of the PA gel platform 14.

Figure 2:
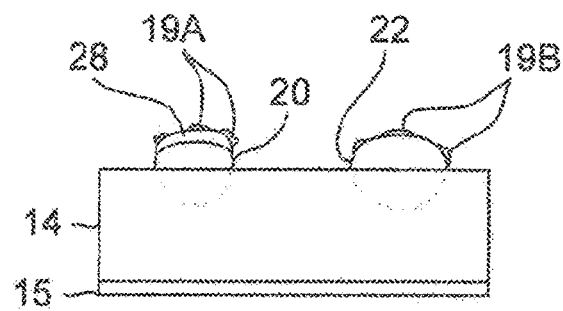
Figure 3:
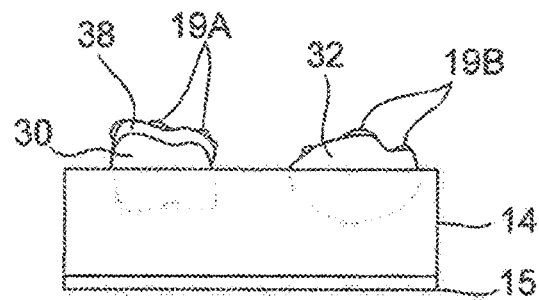

FIG. 2 illustrates curved substrates 20 and 22 disposed in the PA gel platform 14. An additional layer of gel material 28 is disposed on the substrate 20 and the cell 19A grows on the gel material 28. The cell 19B grows directly on the curved substrate 22 with no intervening layer of gel material. FIG. 3 illustrates differently-shaped substrates 30 and 32 disposed in the PA gel platform 14. An additional layer of gel material 38 is disposed on the substrate 30 and the cell 19A grows on the gel material 38. The cell 19B grows directly on the substrate 32 with no intervening layer of gel material.

Figure 4:
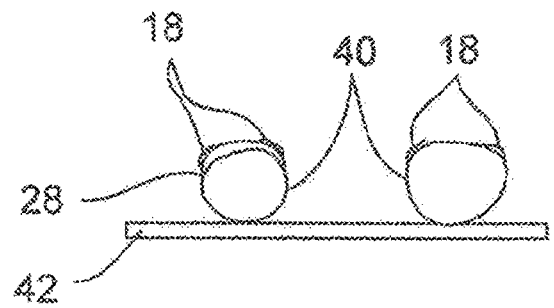

FIG. 4 illustrates an embodiment without the gel platform layer. In this embodiment, the curved substrates 40 are disposed on a material layer 42. An adhesive material (not shown) affixes the substrates 40 to the material layer 42.

The use of a gel for embedding the curved substrate is not required for use in the various described methods and kits herein. Any material layer can be used if it exhibits properties sufficient for receiving and retaining the substrate, such as relatively soft or deformable but yet sufficiently rigid to retain the substrate (e.g., glass balls) in place during cell/tissue culturing. For example, in lieu of the gel 58 of FIG. 5, the material layer may comprise any other material such as glass, plastic, polydimethylsiloxane (PDMS), silica, silicon, silicon nitride, composite materials, transparent materials, non-transparent materials, or any other material suitable for use as the material layer in cell and tissue culturing or in any other surface interface applications. The substrates may comprise the same material as the material layer and emerge or extend from the material layer to form curved structures for cell or tissue culturing or for use in other surface interface applications.

In another aspect, the present disclosure provides methods of cell sorting, comprising culturing a mixed population of cell types, the mixed population comprising a target cell and a non-target cell, on a curved substrate in the presence of cell culture media for a time sufficient for one of a target or a non-target cell to attach to the substrate; and removing, or separating, the cell culture media from the curved substrate, wherein the target cell is contained either in the cell culture media or on the curved substrate, wherein the non-target cell is contained in the cell culture media if the target cell is contained on the curved substrate or the non-target cell is contained on the curved substrate if the target cell is contained in the cell culture media.

The target cell type will be one cell type, while the non-target cell type can be one or more types. Non-limiting examples include: the target cell can be a human mesenchymal stem cell (hMSC) and the non-target cells can include, inter alia, a pool of NIH 3T3 fibroblasts and mouse kidney fibroblasts; the target cell can be a hMSC and the non-target cells can include a pool of NIH 3T3 fibroblasts and mouse kidney fibroblasts and human umbilical vein endothelial cells (HUVEC); the target cell can be NIH 3T3 fibroblasts and the non-target cells can include a pool of hMSCs and human embryonic stem cells (hESC). In some embodiments, the non-target cell can attach to the curved substrate and the target cell is present in the cell culture media. In an alternative embodiment, the target cell can attach to the curved substrate and the non-target cell is present in the cell culture media.

In embodiments comprising a spherical substrate, the substrate may have a diameter less than about 500 µm. In alternative embodiments, the spherical substrate comprises a diameter of about 300 µm or less. In further embodiments, the spherical substrate comprises a diameter greater than about 500 µm.

In some embodiments, the target cell is a stem cell. The stem cells may include embryonic stem cells, tissue-specific stem cells, mesenchymal stem cells, and pluripotent stem cells. In at least one embodiment, the stem cell may be a mesenchymal stem cell.

In some embodiments, the mixed population of cell types comprises at least stem cells and fibroblasts. In one particular embodiment, the fibroblasts attach to the curved substrate and the stem cells do not attach to the curved substrate. In an alternative embodiment, the stem cells attach to the curved substrate and the fibroblasts do not attach to the curved substrate.

Particularly useful in the cell sorting aspects described, the curved substrate may comprise a coating selected from the group consisting of a cell adhesive, a cell adhesion-promotor, a cell repellant, or a combination thereof. The entire or part of the surface of the curved substrate can be coated or functionalized by a layer of cell adhesives or cell adhesion-promotors, such as but not limited to, extracellular matrix proteins, fibronectin, collagen, laminin, etc. or a layer of cell repellents such as but not limited to, polyethylene glycol (PEG), etc., to promote or to inhibit the adhesion of the target or non-target cell onto the curved substrate.

The methods of cell sorting involve culturing a mixed population of cell types in the presence of cell culture media and one or more curved substrate. The substrate may be bound or embedded, as described herein, or it may be suspended in cell culture media. Once either the target or non-target cells are given sufficient time to bind the substrate, the substrate can be separated from the media; the target cell is contained either in the cell culture media or on the curved substrate, wherein the non-target cell is contained in the cell culture media if the target cell is contained on the curved substrate or the non-target cell is contained on the curved substrate if the target cell is contained in the cell culture media.

As one will understand from the provided disclosure herein, whether a target cell or non-target cell binds the substrate will depend both on the types of cells being separated and on the degree of curvature of the substrate. For example, the diameter ranges of the curved substrates (for spherical substrates) will dictate which cell types will attach and which will not attach. For example, hMSCs do not attach to the spherical substrate if the diameter is about 300 µm or less. hMSCs may attach if the spherical substrate has a diameter greater than about 500 µm. Further, at least certain fibroblasts, such as NIH-3T3 cells, attach to spherical substrates great than about 58 µm.

In another aspect, the disclosure provides methods for guided induction of stem cell differentiation, comprising culturing a stem cell on a curved substrate in the presence of cell culture media. As previously described herein, the curved substrate may be a convex substrate, a concave substrate, a spherical substrate, an oval substrate, an elliptical substrate, or combinations thereof. The curved substrate can also include a coating, such as a cell adhesive, a cell adhesion-promotor, a cell repellent, or combinations thereof. The entire or part of the surface of the curved substrate can be coated or functionalized by a layer of cell adhesives or cell adhesion-promotors, such as but not limited to, extracellular matrix proteins, fibronectin, collagen, laminin, etc. or a layer of cell repellents such as but not limited to, polyethylene glycol (PEG), etc., to promote or to inhibit the adhesion of the target or non-target cell onto the curved substrate. Further, the coating can include one or more cell differentiation factors to work in concert with the effects of the curved substrate on the induction of differentiation. Differentiation induction factors or growth factors or soluble factors may be included in the media utilized for culturing the cells either concurrently in the presence of the curved substrate, or, alternatively, before or after culturing of the cells on the curved substrate.

In embodiments comprising a spherical substrate, the spherical substrate may have a diameter of between about 500 µm and about 6 mm; between about 500 µm and about 4 mm; between about 4 mm and about 6 mm; or between about 500 µm and about 2 mm. The diameter of the spherical substrate that is utilized will depend on the type of stem cell that is being differentiated and/or the targeted type of differentiation response that is desired.

The stem cells that are being differentiated by the methods described may include embryonic stem cells, tissue-specific stem cells, mesenchymal stem cells, and pluripotent stem cells. In at least one embodiment, the stem cell may be a mesenchymal stem cell. In some embodiments, the cell culture media may include osteocyte differentiation induction media, whereby the stem cell differentiates into an osteocyte. In other embodiments, the methods result in the stem cell differentiating into an adipocyte.

In various other aspects, the present disclosure provides kits for performing the methods described herein. A kit can comprise a curved substrate and one or more containers comprising at least one reagent. Methods of the disclosure can be carried out using kits described herein for qualitatively or quantitatively sorting cells, directing cell attachment and/or spreading on a substrate, guiding stem cell differentiation, or inducing isotropic spreading of cells.

In one aspect, the present disclosure provides kits for cell sorting, comprising a first reagent, wherein the first reagent comprises a curved substrate. As previously described herein, the curved substrate can be a convex substrate, a concave substrate, a spherical substrate, an oval substrate, an elliptical substrate, or combinations thereof. When the substrate is a spherical substrate, the spherical substrate may include a diameter less than about 500 μm.

In further aspects, the disclosure provides kits for directing cell attachment and spreading on a substrate or inducing isotropic spreading of cells, comprising a first reagent, wherein the first reagent comprises a curved substrate as previously described herein. In embodiments where the curved substrate is spherical, the diameter may be between about 500 μm and about 6 mm or between about 500 μm and about 2 mm or between about 4 mm and about 6 mm or between about 4 mm and about 6 mm. In some embodiments, the curved substrate is at least partially embedded in a gel surface for allowing a cell to isotropically spread over the curved substrate and onto the gel surface.

In yet another aspect, the disclosure provides kits for guided induction of stem cell differentiation, comprising a first reagent, wherein the first reagent comprises a curved substrate. In embodiments where the substrate is spherical, the substrate may have a diameter of between about 500 μm and about 6 mm or between about 500 μm and about 2 mm or between about 4 mm and about 6 mm or between about 4 mm and about 6 mm.

The curved substrate in the kits disclosed above can be provided as a component of any structure herein described, such as for example, curved substrates embedded in a gel surface, or as a plurality of curved substrates suspended in a reagent. The reagent can be, for example, cell culture media. The kit can also contain a solid support such as microtiter multi-well plates, standards, assay diluent, wash buffer, adhesive plate covers, and/or instructions for carrying out a method of the disclosure using the kit. Likewise, the curved substrate can include one or more coatings, such as a cell adhesive, a cell adhesion-promotor, a cell repellent, or a combination thereof. The entire or part of the surface of the curved substrate can be coated or functionalized by a layer of cell adhesives or cell adhesion-promotors, such as but not limited to, extracellular matrix proteins, fibronectin, collagen, laminin, etc. or a layer of cell repellents, such as but not limited to, polyethylene glycol (PEG), etc., to promote or to inhibit the adhesion of the target or non-target cell(s) onto the curved substrate. For the cell differentiation kits, the substrate may also include a coating containing one or more cell-differentiation factor. Differentiation induction factors or growth factors or soluble factors may be included in the media utilized for culturing the cells either concurrently in the presence of the curved substrate, or, alternatively, before or after culturing of the cells on the curved substrate.

Kits of the disclosure include reagents for use in the methods described herein, in one or more containers. The reagents can include cell culture media, cell-type detection or labelling agents, and stem cell differentiation media. The kits may include specific internal controls, and/or probes, buffers, and/or excipients, separately or in combination. Each reagent can be supplied in a solid form or liquid buffer that is suitable for inventory storage. Kits may also include means for obtaining a sample from a host organism or an environmental sample, such as for example components for extracting cell populations containing stem cells and/or fibroblasts.

Kits of the disclosure can be provided in suitable packaging. Such packaging materials include glass and plastic (e.g., polyethylene, polypropylene, and polycarbonate) bottles, vials, paper, plastic, and plastic-foil laminated envelopes and the like. In certain embodiments, the kit includes a microtiter tray with two or more wells and with reagents including primers, probes, specific internal controls, and/or molecular beacons in the wells.

Kits of the disclosure may optionally include a set of instructions in printed or electronic (e.g., magnetic or optical disk) form, relating information regarding the components of the kits and/or how to make various determinations (e.g., substrate binding to target cells, comparison to control standards, etc.). The kit may also be commercialized as part of a larger package that includes instrumentation for measuring other biochemical components.

Certain aspects of the disclosure provide the following non-limiting embodiments:

Embodiment 1

A method of cell sorting, comprising: culturing a mixed population of cell types, the mixed population comprising a target cell and a non-target cell, on a curved substrate in the presence of cell culture media for a time sufficient for one of a target or a non-target cell to attach to the substrate; and removing, or separating, the cell culture media from the curved substrate, wherein the target cell is contained either in the cell culture media or on the curved substrate, wherein the non-target cell is contained in the cell culture media if the target cell is contained on the curved substrate or the non-target cell is contained on the curved substrate if the target cell is contained in the cell culture media.

Embodiment 2

The method of Embodiment 1, wherein the non-target cell attaches to the curved substrate and the target cell is present in the cell culture media.

Embodiment 3

The method of Embodiment 1, wherein the target cell attaches to the curved substrate and the non-target cell is present in the cell culture media.

Embodiment 4

The method of Embodiments 1-3, wherein the curved substrate comprises an array or arrays of curved substrates.

Embodiment 5

The method of Embodiments 1-4, wherein the target cell is a stem cell.

Embodiment 6

The method of Embodiment 5, wherein the stem cell is a mesenchymal stem cell.

Embodiment 7

The method of Embodiments 1-6, wherein the curved substrate is selected from the group consisting of a convex substrate, a concave substrate, a spherical substrate, an oval substrate, an elliptical substrate, and combinations thereof.

Embodiment 8

The method of Embodiment 1, wherein the curved substrate is a spherical substrate.

Embodiment 9

The method of Embodiment 8, wherein the spherical substrate is a ball.

Embodiment 10

The method of Embodiment 9, wherein the ball is a glass ball.

Embodiment 11

The method of Embodiment 8, wherein the spherical substrate comprises a diameter less than about 500 µm.

Embodiment 12

The method of Embodiment 1, wherein the mixed population of cell types comprises stem cells and fibroblasts.

Embodiment 13

The method of Embodiment 1, wherein the mixed population of cell types consists of stem cells and fibroblasts.

Embodiment 14

The method of Embodiment 12, wherein the fibroblasts attach to the curved substrate and the stem cells do not attach to the curved substrate.

Embodiment 15

The method of Embodiment 13, wherein the fibroblasts attach to the curved substrate and the stem cells do not attach to the curved substrate.

Embodiment 16

The method of Embodiment 12, wherein the stem cells attach to the curved substrate and the fibroblasts do not attach to the curved substrate.

Embodiment 17

The method of Embodiment 13, wherein the stem cells attach to the curved substrate and the fibroblasts do not attach to the curved substrate.

Embodiment 18

The method of Embodiment 8, wherein the spherical substrate comprises a diameter of about 300 µm or less.

Embodiment 19

The method of Embodiments 1-18, wherein the curved substrate comprises a coating selected from the group consisting of a cell adhesive, a cell adhesion-promotor, a cell repellent, or a combination thereof.

Embodiment 20

The method of Embodiment 1, wherein the non-target cell type is one or more cell types.

Embodiment 21

A kit for cell sorting, comprising: a first reagent, wherein the first reagent comprises a curved substrate.

Embodiment 22

The kit of Embodiment 21, wherein the curved substrate is selected from the group consisting of a convex substrate, a concave substrate, a spherical substrate, an oval substrate, an elliptical substrate, and combinations thereof.

Embodiment 23

The kit of Embodiments 21-22, wherein the curved substrate comprises a spherical substrate.

Embodiment 24

The kit of Embodiment 23, wherein the spherical substrate comprises a diameter less than about 500 µm.

Embodiment 25

The kit of Embodiments 21-24, wherein the curved substrate comprises a coating selected from the group consisting of a cell adhesive, a cell adhesion-promotor, a cell repellent, or a combination thereof.

Embodiment 26

A kit for cell sorting, comprising: a first reagent, wherein the first reagent comprises a spherical substrate having a diameter less than about 500 µm.

Embodiment 27

The kit of Embodiment 26, wherein first reagent is immobilized on a solid support.

Embodiment 28

The kit of Embodiments 26-27, further comprising a second reagent, wherein the second reagent comprises cell culture media.

Embodiment 29

The kit of Embodiments 26-28, further comprising a third reagent, wherein the third reagent comprises a detection or labelling agent.

Embodiment 30

The kit of Embodiments 26-29, wherein the spherical substrate comprises a coating selected from the group consisting of a cell adhesive, a cell adhesion-promotor, a cell repellent, or a combination thereof.

Embodiment 31

A method of directing cell attachment and spreading on a substrate, comprising: culturing a cell on a curved substrate in the presence of cell culture media, wherein attachment and spreading increases as the curvature of the substrate decreases.

Embodiment 32

The method of Embodiment 31, wherein the curved substrate is selected from the group consisting of a convex substrate, a concave substrate, a spherical substrate, an oval substrate, an elliptical substrate, and combinations thereof.

Embodiment 33

The method of Embodiments 31-32, wherein the curved substrate comprises a coating selected from the group consisting of a cell adhesive, a cell adhesion-promotor, a cell repellent, or a combination thereof.

Embodiment 34

The method of Embodiments 32-33, wherein the curved substrate is a spherical substrate, wherein the attachment and spreading increases as the diameter of the spherical substrate increases.

Embodiment 35

The method of Embodiment 34, wherein the spherical substrate comprises a diameter of between about 500 µm and about 6 mm, wherein attachment and spreading is influenced in that both attachment and spreading increases as the diameter of the spherical substrate increases from about 500 µm to about 6 mm.

Embodiment 36

A kit for directing cell attachment and spreading on a substrate, comprising: a first reagent, wherein the first reagent comprises a curved substrate.

Embodiment 37

The kit of Embodiment 36, wherein the curved substrate is selected from the group consisting of a convex substrate, a concave substrate, a spherical substrate, an oval substrate, an elliptical substrate, and combinations thereof.

Embodiment 38

The kit of Embodiments 36-37, wherein the curved substrate comprises a coating selected from the group consisting of a cell adhesive, a cell adhesion-promotor, a cell repellent, or a combination thereof.

Embodiment 39

The kit of Embodiment 36, wherein the curved substrate is a spherical substrate.

Embodiment 40

The kit of Embodiment 39, wherein the spherical substrate comprises a diameter of between about 500 µm and about 6 mm.

Embodiment 41

The kit of Embodiments 36-40, wherein first reagent is immobilized on a solid support.

Embodiment 42

The kit of Embodiments 36-41, further comprising a second reagent, wherein the second reagent comprises cell culture media.

Embodiment 43

The kit of Embodiment 42, wherein the cell culture media is a culture media that induces stem cell differentiation.

Embodiment 44

The kit of Embodiments 36-44, further comprising a third reagent, wherein the third reagent comprises a cell-type detection agent.

Embodiment 45

The kit of Embodiment 39, wherein the spherical substrate comprises a diameter of between about 500 µm and about 2 mm.

Embodiment 46

The kit of Embodiment 39, wherein the spherical substrate comprises a diameter of between about 2 mm and about 4 mm.

Embodiment 47

The kit of Embodiment 39, wherein the spherical substrate comprises a diameter of between about 4 mm and about 6 mm.

Embodiment 48

A method for guided induction of stem cell differentiation, comprising: culturing a stem cell on a curved substrate in the presence of cell culture media.

Embodiment 49

The method of Embodiment 48, wherein the curved substrate comprises a coating selected from the group consisting of a cell adhesive, a cell adhesion-promotor, a cell repellent, or a combination thereof.

Embodiment 50

The method of Embodiments 48-49, wherein the curved substrate is selected from the group consisting of a convex substrate, a concave substrate, a spherical substrate, an oval substrate, an elliptical substrate, and combinations thereof.

Embodiment 51

The method of Embodiment 48, wherein the curved substrate is a spherical substrate.

Embodiment 52

The method of Embodiment 51, wherein the spherical substrate comprises a diameter of between about 500 µm and about 4 mm.

Embodiment 53

The method of Embodiment 51, wherein the spherical substrate comprises a diameter of between about 500 µm and about 2 mm.

Embodiment 54

The method of Embodiment 51, wherein the spherical substrate comprises a diameter of between about 4 mm and about 6 mm.

Embodiment 55

The method of Embodiment 51, wherein the spherical substrate comprises a diameter of between about 500 µm and about 6 mm.

Embodiment 56

The method of Embodiment 48, wherein the stem cell is a mesenchymal stem cell.

Embodiment 57

The method of Embodiment 56, wherein the cell culture media comprises osteocyte differentiation induction media, whereby the stem cell differentiates into an osteocyte.

Embodiment 58

The method of Embodiment 56, wherein the stem cell differentiates into an adipocyte.

Embodiment 59

A kit for guided induction of stem cell differentiation, comprising: a first reagent, wherein the first reagent comprises a curved substrate.

Embodiment 60

The kit of Embodiment 59, wherein the curved substrate is selected from the group consisting of a convex substrate, a concave substrate, a spherical substrate, an oval substrate, an elliptical substrate, and combinations thereof.

Embodiment 61

The kit of Embodiments 59-60, wherein the curved substrate comprises a coating selected from the group consisting of a cell adhesive, a cell adhesion-promotor, a cell repellent, or a combination thereof.

Embodiment 62

The kit of Embodiment 59, wherein the curved substrate is a spherical substrate.

Embodiment 63

The kit of Embodiment 62, wherein the spherical substrate comprises a diameter of between about 500 µm and about 6 mm.

Embodiment 64

The kit of Embodiments 59-63, wherein first reagent is immobilized on a solid support.

Embodiment 65

The kit of Embodiments 59-64, further comprising a second reagent, wherein the second reagent comprises cell culture media.

Embodiment 66

The kit of Embodiment 65, wherein the cell culture media is a culture media that induces stem cell differentiation.

Embodiment 67

The kit of Embodiments 59-66, further comprising a third reagent, wherein the third reagent comprises a cell-type detection agent.

Embodiment 68

The kit of Embodiment 62, wherein the spherical substrate comprises a diameter of between about 500 µm and about 2 mm.

Embodiment 69

The kit of Embodiment 62, wherein the spherical substrate comprises a diameter of between about 2 mm and about 4 mm.

Embodiment 70

The kit of Embodiment 62, wherein the spherical substrate comprises a diameter of between about 4 mm and about 6 mm.

Embodiment 71

A method of inducing isotropic spreading of cells, comprising: culturing a cell on a curved substrate, the curved substrate partially embedded in a gel surface, wherein the cell isotropically spreads over the curved substrate and onto the gel surface.

Embodiment 72

The method of Embodiment 71, wherein the curved substrate comprises a coating selected from the group consisting of a cell adhesive, a cell adhesion-promotor, a cell repellent, or a combination thereof.

Embodiment 73

The method of Embodiment 71, wherein the curved substrate is a spherical substrate.

Embodiment 74

The method of Embodiment 73, wherein the spherical substrate comprises a diameter of between about 5 µm and about 100 µm.

Embodiment 75

The method of Embodiment 71, wherein the curved substrate is selected from the group consisting of a convex substrate, a concave substrate, a spherical substrate, and combinations thereof.

Embodiment 76

A kit for inducing isotropic spreading of cells, comprising: a first reagent, wherein the first reagent comprises a curved substrate.

Embodiment 77

The kit of Embodiment 76, wherein the curved substrate is at least partially embedded in a gel surface, for allowing a cell to isotropically spread over the curved substrate and onto the gel surface.

Embodiment 78

The kit of Embodiment 76, wherein the curved substrate is selected from the group consisting of a convex substrate, a concave substrate, a spherical substrate, and combinations thereof.

Embodiment 79

The kit of Embodiments 76-78, wherein the curved substrate comprises a coating selected from the group consisting of a cell adhesive, a cell adhesion-promotor, a cell repellent, or a combination thereof.

Embodiment 80

A method of inducing isotropic spreading of cells, comprising: culturing a cell on a curved substrate, the curved substrate immobilized on a material layer, wherein the cell isotropically spreads over the curved substrate and onto the material layer.

Embodiment 81

The method of Embodiment 80, wherein the curved substrate is a spherical substrate.

Embodiment 82

The method of Embodiment 81, wherein the spherical substrate comprises a diameter of between about 5 µm and about 100 µm.

Embodiment 83

The method of Embodiment 80, wherein the curved substrate is selected from the group consisting of a convex substrate, a concave substrate, a spherical substrate, an oval substrate, an elliptical substrate, and combinations thereof.

Embodiment 84

The method of Embodiment 83, wherein the curved substrate is a spherical substrate.

Embodiment 85

The method of any of Embodiments 80-84, wherein the curved substrate comprises a coating selected from the group consisting of a cell adhesive, a cell adhesion-promotor, a cell repellent, or a combination thereof.

The methods and devices herein described and the related kits are further illustrated in the following examples, which are provided by way of illustration and is not intended to be limiting. It will be appreciated that variations in proportions and alternatives in elements of the components shown will be apparent to those skilled in the art and are within the scope of embodiments of the present disclosure. Theoretical aspects are presented with the understanding that Applicant does not seek to be bound by the theory presented. All percentages, unless otherwise specified, are by weight, and all solvent mixture proportions are by volume unless otherwise noted.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods, devices, and related kits herein described are further illustrated in the following examples, which are provided by way of illustration and are not intended to be limiting. It will be appreciated that variations in proportions and alternatives in elements of the components shown will be apparent to those skilled in the art and are within the scope of aspects and embodiments of the present disclosure. Theoretical aspects are presented with the understanding that Applicants do not seek to be bound by the theory presented. All parts or amounts, unless otherwise specified, are by weight.

The following materials and methods were used for the methods and devices exemplified in Example 1 herein.

RT-PCR Analysis—

To check the differentiation responses of the hMSCs growing on the glass balls, RT-PCR analysis was conducted to quantify the relative gene expression of these hMSCs. After 11 days of growing on the glass balls of the hMSCs in the above-mentioned growth media, the glass balls with the hMSCs attached were extracted with tweezers and put into a 1.5 ml epi tube. The time 11 days is long enough for the differentiation gene expression of the hMSCs to occur in accordance with the relevant time frames reported in the literature (Engler et al., 2006; Viswanathan et al., 2015; Kilian et al., 2010). 1 ml of Trizol (TriReagent, Molecular Research Center TR118, Cincinnati, Ohio) was added to the epi tube for 0.5-1×106 cells to lyse the cell membrane. To separate the phases, 0.2 ml of chloroform (Sigma-Aldrich C2432, St. Louis, Mo.) was added into the tube. After shaken vigorously, the tube was centrifuged at 12,000 rpm and 4° C. for 20 min. The top clear aqueous phase layer containing RNA was then transferred to a new 1.5 mL epi tube. To precipitate the RNA, 0.5 ml of isopropyl alcohol (Sigma-Aldrich 19516, St. Louis, Mo.) was added into the tube. After inverted several times, the tube was incubated at room temperature for 20 min and then was centrifuged at 12,000 rpm and 4° C. for 20 min. The solution was slowly poured out with the help of a pipette. To wash the pellet of the RNA, 1 ml of 75% ethanol (Sigma-Aldrich E7023, St. Louis, Mo.) was added into the tube, and then the tube was centrifuged at 12,000 rpm and 4° C. for 20 min. The ethanol was slowly poured out with the help of a pipette, and then 16 μL of DNAse-RNAse free water (DEPC water, VWR IC821739, Radnor, Pa.) was added into the tube to dissolve the RNA pellet. The tube was left on a heat block at 55° C. for 5 min for the pellet to become invisible.

The quality and concentration of the RNA samples were then assessed by using a spectrophotometer (NanoDrop LITE, Thermo Scientific ND-NDL, Waltham, Mass.). To assess the purity of an RNA sample, one must evaluate the value of A260/A280 following the spectrophotometer reading. The value of A260/A280 should be greater than 2.0 if the RNA sample is pure enough. Lower values indicate the presence of contaminants such as salts, carbohydrates, peptides, and proteins. In order to reveal the differences in the relative gene expression results of the hMSCs growing on the glass balls with different diameters, it is critical to use the same amount of the corresponding RNA sample in each cDNA synthesis reaction, which was conducted by using the iScript cDNA Synthesis Kit (Bio-RAD 170, Hercules, Calif.) according to the manufacturer's instruction. The complete cDNA reaction mix (total volume: 20 μL) was incubated in a thermal cycler (T100, Bio-RAD 1861096, Hercules, Calif.) by using a protocol recommended by the manufacturer.

The quantitative PCR (qPCR) reaction mix (total volume: 20 μL) consists of an appropriate amount of the synthesized cDNA (1-4 μL), a selected primer (1 μL) to target the specific type of gene expression, the SsoAdvanced Universal SYBR Green Supermix (Bio-RAD 172, Hercules, Calif.) (10 μL), and nuclease-free water. The qPCR reaction mix was loaded into an RT-PCR instrument (CFX Connect Real-Time System, Bio-RAD 1855200, Hercules, Calif.), and the instrument was programmed to run the reaction mix according to the following thermal cycling protocol recommended by the manufacturer: activation at 95° C. for 2 min, then denaturation at 95° C. for 5 sec and annealing/extension at 60° C. for 30 sec for 40 cycles. In the experiment, 18S rRNA (18S ribosomal RNA) was used as the housekeeping gene. The gene expression data were analyzed by using the method, and the gene expression result of the hMSCs growing on the flat glass plates was used as the control to compute the relative gene expression results of the hMSCs growing on the glass balls with different diameters.

The following materials and methods were used for the methods and devices exemplified in Examples 2-4 herein.

Preparation of the Micro Glass Ball Embedded Polyacrylamide (PA) Gels—

The micro glass ball embedded PA gels were prepared by using the protocol described by the inventor earlier (Lee and Yang, 2012) (incorporated herein by reference in its entirety), and the Young's modulus of a PA gel was determined by using the protocol of Wang and Pelham on the PA gel preparation (Wang and Pelham, 1998). PA gels with a wide range of the Young's modulus can be prepared by adjusting the concentrations of acrylamide and bis-acrylamide (the cross-linker) in the final PA solution. For the presented study, the final concentrations of 8% w/v acrylamide and 0.08% w/v bis-acrylamide were used to form the PA gels with the Young's modulus of 75 kPa, the final concentrations of 8% w/v acrylamide and 0.02% w/v bis-acrylamide were used to form the PA gels with the Young's modulus of 10 kPa, and the final concentrations of 3% w/v acrylamide and 0.10% w/v bis-acrylamide were used to form the PA gels with the Young's modulus of 1 kPa. To prepare the PA gels with one of the above-mentioned three Young's moduli, the PA solution with a final volume of 5,000 μL was prepared by mixing appropriate amounts of the 40% w/v acrylamide stock solution and the 2% w/v bis-acrylamide stock solution with deionized water, and then the PA solution was degased by vacuuming for 20 minutes. To polymerize the PA solution, 30 μL of N,N,N',N'-tetramethyl-ethylenediamine (TEMED, Fisher BioReagents BP150-20, Pittsburgh, Pa.) was added to the PA solution. The PA solution was then immediately divided into five 15 mL tubes as 1,000 μL per tube. After 11 μL of 10% ammonium persulfate (Electrophoresis, Fisher BioReagents BP179-25, Pittsburgh, Pa.) was added to each tube of the PA solution, the PA solution started to polymerize within one min, and this polymerization process finished in about 24 hours.

Before the polymerization process started, 100 μL of the PA solution was pipetted onto the bottom of a 35 mm-diameter cell culture dish, and then an appropriate amount of the micro glass balls with diameters of mixed 5-100 μm (3M Glass bubbles K-20, St. Paul, Minn.) was immediately dropped onto the PA solution. A 22 mm-diameter glass coverslip was then carefully placed on the top of the PA solution to evenly press the micro glass balls into the unpolymerized PA solution. After the polymerization process of the PA solution completed in about 24 hours, the micro glass ball embedded PA gel was formed. The surface of the micro glass ball embedded PA gel was then coated with the cell adhesive protein, fibronectin (Sigma-Aldrich F8141-1MG, St. Louis, Mo.).

Cell Culture—

NIH-3T3 mouse embryo fibroblasts (ATCC CRL-1658, Manassas, Va.) were cultured, on the above-prepared micro glass ball embedded PA gels in the cell culture dishes, in Dulbecco's Modified Eagle Medium (DMEM, ATCC 30-2002, Manassas, Va.) with 10% Calf Bovine Serum (ATCC 30-2030, Manassas, Va.) and 1% Penicillin-Streptomycin (MP biomedicals no. 091670049, Solon, Ohio). The fibroblasts were incubated at 37° C. with a humidified 5% $CO_2$ atmosphere, and the culture medium was changed twice per week.

Imaging Analysis—

Phase-contrast images of the cells wrapping over the micro glass balls in the above cell culture were taken by an upright light microscope (Axioskop 2 plus, Carl Zeiss, Germany) using 10× and 40× objectives. The phase-contrast images were manually outlined to define the boundaries of the cells to measure the spread areas of the cells by using the software ImageJ.

The following materials and methods were used for the methods and devices exemplified in Examples 5-8 herein.

Treatment of Glass Coverslips—

In a micro glass ball embedded gel for the purpose of this study, the upper parts of many of the micro glass balls are exposed from the top surface of the gel. When a micro glass ball embedded gel experimental platform is prepared, the platform is subjected to the perturbing fluidic shear forces of the gel solution and phosphate buffered saline (PBS) during the handlings and transportations of the platform. When the platform is used for cell culturing, the platform is subjected to the perturbing fluidic shear forces of the culture media during the handlings and transportations of the culture dish, loaded with the platform, in the entire cell culturing, treatment, observation, and imaging process. These inevitable perturbing fluidic shear forces induce rolling and detaching of the embedded micro glass balls from the gel. Thus, the most important issue of using a micro glass ball embedded PA gel experimental platform for cell studies is how to reduce the rolling and detaching of the embedded micro glass balls from the PA gel during the entire this platform-related experimental process.

It is well known that a polymer network swells at temperatures higher than the room temperature and shrinks at temperatures lower than the room temperature (Tanaka et al., 1992). A PA gel shrinks in water at sufficiently low temperatures and swell at higher temperatures, slowly and reversibly. The extents of the shrinking and swelling and the inverting temperatures between these two processes depend on the gel composition (Hirotsu, 1987; Beltran et al., 1991). It was observed that the PA gels were significantly swollen at 37° C. in the incubator compared with the same PA gels at room temperature, and these volume changes of the PA gels loosened the adhesion between the embedded micro glass balls and the PA gel materials, and then the embedded micro glass balls became much more susceptible to the above-mentioned perturbing fluidic shear forces that drove the rolling and detaching of the embedded micro glass balls from the PA gels during the entire cell culturing process. Thus, to reduce the rolling and detaching of the embedded micro glass balls from a PA gel, the volume change of the PA gel during the entire experimental process needs to be reduced as much as possible.

In order to reduce the volume changes of the PA gels, glass coverslips were treated with allytrichlorosilane (ATCS) to present vinyl groups on the surfaces of the glass coverslips to promote and strengthen the attachment of the PA gels to the glass coverslips. The vinyl groups in ATCS react with the acrylamide during the free radical polymerization of the PA solution, and then the PA gels adhere strongly to the ATCS functionalized surfaces of the glass coverslips by covalent bindings (Buxboim et al., 2010). This strong adherence of the PA gels to the ATCS treated glass coverslips will ensure the volume changes of the PA gels to be minimum during the entire experimental process, and thus the PA gels can hold the micro glass balls tightly and any rolling and detaching of the embedded micro glass balls from the PA gels are minimized. A brief introduction of the ATCS treating process on the glass coverslips is as follows.

Glass coverslips of 22 mm in diameter were boiled in ethanol for 10 minutes, rinsed in distilled water (DW), and immersed in RCA at 80° C. for 10 minutes. RCA consists of DW, hydrogen peroxide (30%, Fisher BioReagents BP2633-500, Pittsburgh, Pa.), and ammonium hydroxide (29%, Fisher BioReagents S93120A, Pittsburgh, Pa.) at a volume ratio of 3:1:1. The RCA-treated glass coverslips were rinsed in DW, ethanol (Fisher BioReagents A407-1, Pittsburgh, Pa.), and chloroform (Fisher BioReagents AC15821-0010, Pittsburgh, Pa.), and silanized in 0.1% ATCS (95%, Fisher BioReagents AC31322-0050, Pittsburgh, Pa.) in chloroform with 0.1% triethylamine (TEA, 99.7%, Fisher BioReagents AC21951-0050, Pittsburgh, Pa.) for 30 min. The ATCS treated glass coverslips were subsequently rinsed in chloroform, ethanol, and DW, and then these coverslips were immediately used for the preparation of the micro glass ball embedded PA gels on their top surfaces.

Preparation of PA Gels—

Due to their smaller volume changes, the more rigid PA gels can also do a better job than the relatively softer PA gels in reducing the rolling and detaching of the embedded micro glass balls from the PA gels during the entire experimental process. To make the more rigid PA gels (Lee and Yang, 2012; Wang and Pelham, 1998), a 1500 µL of acrylamide solution (40%/electrophoresis, Fisher BioReagents BP1402-1, Pittsburgh, Pa.) and a 700 µL of bis-acrylamide solution (2%/electrophoresis, Fisher BioReagents BP1404-250, Pittsburgh, Pa.) were mixed in a 2750 µL of deionized water with a 50 µL of HEPES buffer solution (1M/pH7.3, Fisher BioReagents BP299-100, Pittsburgh, Pa.) to form the PA solution. The total volume of 5,000 µL of the PA solution was de-gassed by vacuuming for 20 minutes. To polymerize the PA solution, a 30 µL of N,N,N',N'-tetramethyl-ethylenediamine (TEMED, Fisher BioReagents BP150-20, Pittsburgh, Pa.) was added to the PA solution. Then the PA solution was immediately divided into five 15-mL tubes as 1,000 µL per tube. After adding an 11 µL of 10% ammonium persulfate (Electrophoresis, Fisher BioReagents BP179-25, Pittsburgh, Pa.) to each tube of the PA solution, the PA solution starts to polymerize within one min, and this polymerization process finishes in about 24 hours. After the polymerization process is finished, the formed PA gels should have elastic moduli that are much larger than 100 kPa according to Wang and Pelham's protocol (Wang and Pelham, 1998) for the concentrations of the acrylamide solution and bis-acrylamide solution used here.

Before the polymerization process starts, a volume of the PA solution, depending on the diameters of the glass balls to be embedded, was pipetted onto an ATCS treated glass coverslip lying on the bottom of a 35 mm-diameter cell culture dish. Depending on the desired studies, appropriate amounts or combination of the micro glass balls with diameters of mixed 5-100 µm, mixed 50-300 µm, 500 µm, 750 µm, 900 µm, 1.1 mm, 2 mm, 3 mm, and 4 mm (Blockheadstamps, Portland, Oreg.) were immediately dropped onto the PA solution. A 22 mm-diameter glass coverslip was then carefully placed on the top of the PA solution to evenly press the glass balls into the unpolymerized PA solution. The polymerization process of the PA solution completed in about 24 hours, and the micro glass ball embedded PA gel, which was attached to the ATCS treated glass coverslip, was formed. The formed micro glass ball embedded PA gel was rinsed with PBS twice in the following 24 hours. After removing all the PBS in the cell culture dish, the micro glass ball embedded PA gel was dried in air and exposed to the ultraviolet radiation existing in the cell culture hood for 2 hours for sterilization.

Cell Culture—

NIH-3T3 mouse embryo fibroblasts (ATCC CRL-1658, Manassas, Va.) were cultured, in the cell culture dishes loaded with the glass coverslips with the above-prepared micro glass ball embedded PA gels attached, in Dulbecco's Modified Eagle Medium (DMEM, ATCC 30-2002, Manassas, Va.) with 4500 mg/L glucose, 4 mM L-glutamine, 1 mM sodium pyruvate, and 1500 mg/L sodium bicarbonate, and the DMEM was supplemented with 10% Calf Bovine Serum (ATCC 30-2030, Manassas, Va.) and 1% Penicillin-Streptomycin (MP biomedicals no. 091670049, Solon, Ohio). The fibroblasts were incubated at 37° C. with a humidified 5% $CO_2$ atmosphere, and the culture medium was changed twice per week.

hMSCs (ATCC PCS-500-011, Manassas, Va.) were cultured, also in the cell culture dishes loaded with the glass coverslips with the above-prepared micro glass ball embedded PA gels attached, in Mesenchymal Stem Cell Basal Media (ATCC PCS-500-030, Manassas, Va.) plus one Mesenchymal Stem Cell Growth Kit (ATCC PCS-500-040, Manassas, Va.) that contains the following growth supplements: MSC Supplement (composed of FB S, rh FGF basic, rh FGF acidic, and rh EGF) and L-alanyl-L-glutamine. Gentamicin-Amphotericin B Solution (ATCC PCS-999-025, Manassas, Va.) with Penicillin-Streptomycin-Amphotericin B Solution (ATCC PCS-999-002, Manassas, Va.) was also added to the basal media. The hMSCs were incubated at 37° C. with a humidified 5% $CO_2$ atmosphere, and the culture medium was changed twice per week.

For comparisons, the above two cell types were also cultured on the flat glass plates, 22 mm-square glass coverslips.

Image Analysis—

Phase-contrast images of the cells adhered to the micro glass balls and the flat glass plates in the above cell culture were taken by an upright light microscope (Axioskop 2 plus, Carl Zeiss, Germany) using a 10× objective. The phase-contrast images were manually outlined to define the boundaries of the cells to measure the lengths, widths, and spread areas of the cells by using the software Photoshop (Adobe Systems Incorporated, San Jose, Calif.) and the software ImageJ (available at http://rsb.info.nih.gov.ij/).

By using the enlarged phase-contrast image of a cell, the boundary of the cell nucleus was reasonably-accurately outlined by an oval. The ex-rectangle of this oval was then sketched, and the four sides of this ex-rectangle were tangent to the oval, the length direction of this ex-rectangle was parallel to the long axis of the oval, and the width direction of this ex-rectangle was parallel to the short axis of the oval. This ex-rectangle was then enlarged with the aspect ratio unchanged to just enclose the entire boundary of the cell. In this paper, the length of this enlarged ex-rectangle was the measure of the cell length. In the directions that are perpendicular to the direction (i.e., the length direction of the ex-rectangle) that measured the cell length, the maximum straight-line distance from one side of the cell boundary to the other side of the cell boundary across the cell body was the measure of the cell width. This method of defining/measuring the length and width of a cell should be a reasonable method to quantify the dimensions of the cell.

The aspect ratio of the cell was then calculated from the measured length and width of the cell and calculated as cell width/length, and the spread area of the cell was measured as the total area enclosed by the boundary of the cell.

Statistical Analysis—

The measured data, including the cell lengths, widths, aspect ratios, and spread areas, were shown as mean±standard deviation (SD) for each ball diameter. The significance or insignificance of differences between the means of the measured spread areas of the cells growing on the glass balls with different diameters were tested by performing the one-way analysis of variance (ANOVA) with Tukey's post hoc test for multiple comparisons by the software SPSS Statistics (International Business Machines (IBM) Corp., Armonk, N.Y.).

Example 1

Stem Cell Differentiation Responses to Substrate Curvatures

Figure 7:
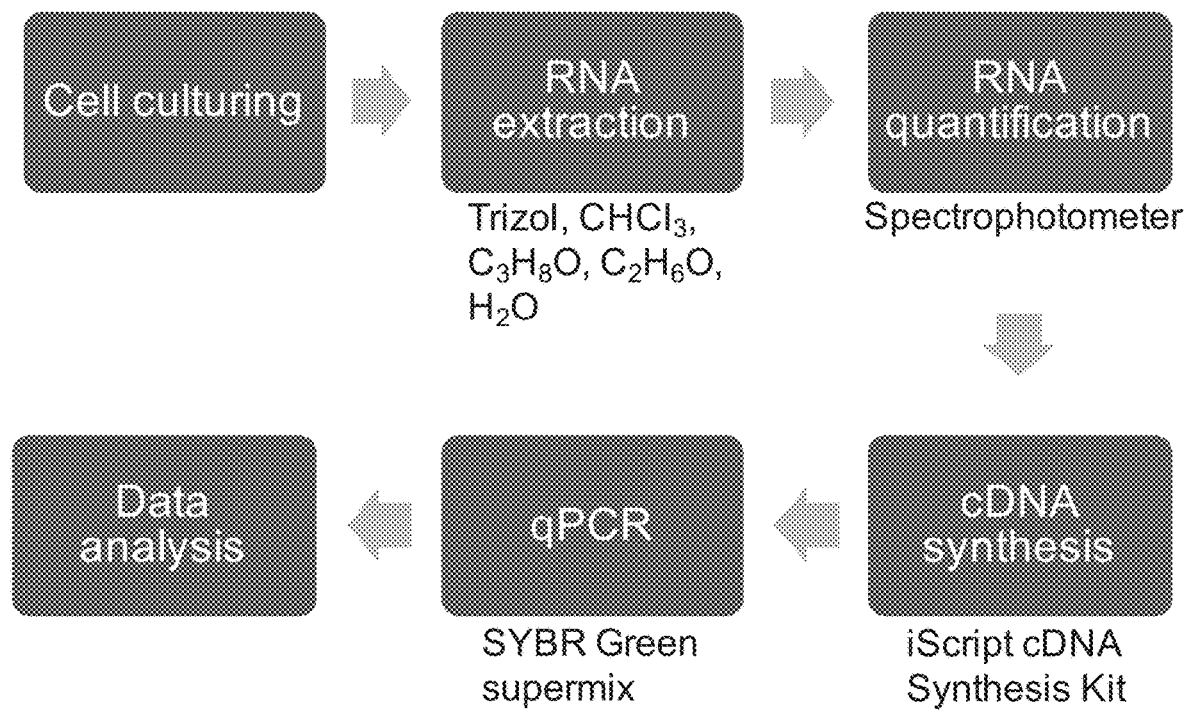
FIG. 7 illustrates gene expression experiments by real-time polymerase chain reaction (RT-PCR or qPCR)
Figure 8:
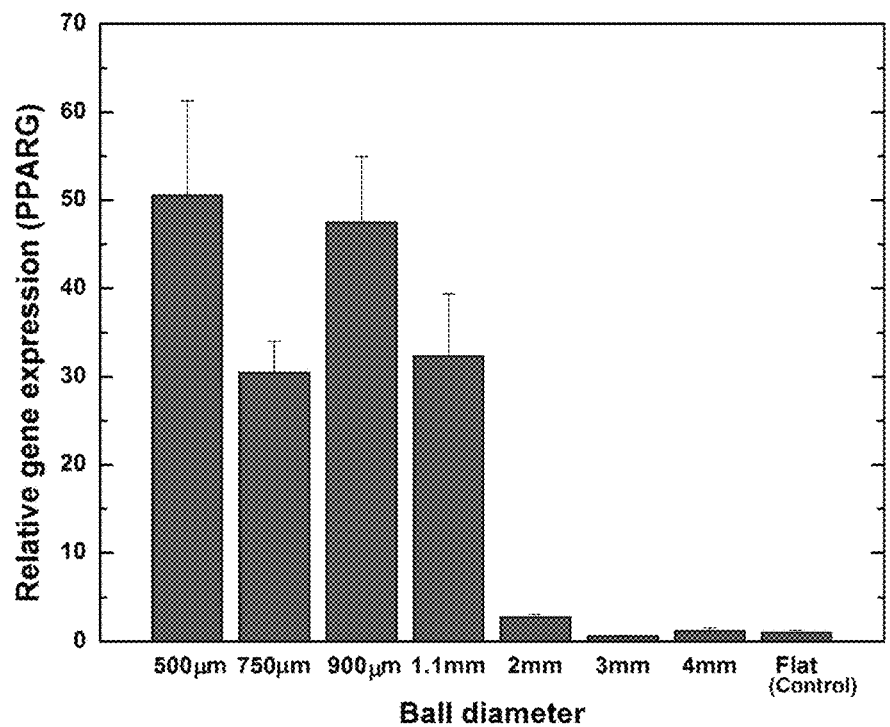
FIG. 8 shows a graph of adipogenesis induced by substrate curvatures. Relative gene expression (PPARG) is graphed relative to ball diameter.

Since the mean cell spreading area decreases with the increase of the substrate curvature, the cell contractility decreases with the increase of the substrate curvature. Therefore, it was hypothesized that the curvature of the substrate on which a stem cell is growing guides the differentiation of the stem cell. Adipose-derived human mesenchymal stem cells (hMSCs) were utilized in the experiments described below, since they are capable of differentiation into various cell types based on the type of differentiation media utilized (see FIG. 6).

hMSCs were cultured without differentiation induction media on the micro glass ball embedded PA gels in the stem cell basal media with growth kit for 11 days before analyzing gene expression (see FIG. 7). Therefore, since no differentiation-induction chemical media was added (involved), the differentiation results are due to substrate curvatures only, as illustrated in FIG. 8.

hMSCs were also cultured with adipocyte differentiation induction media on the micro glass ball embedded PA gels in the stem cell basal media with growth kit for 48 hours. Media was then replaced and incubated with adipocyte differentiation initiation media for 48 hours, and then media was replaced and incubated with adipocyte differentiation maintenance media for 7 days before analyzing gene expression (see FIG. 7).

Figure 9:
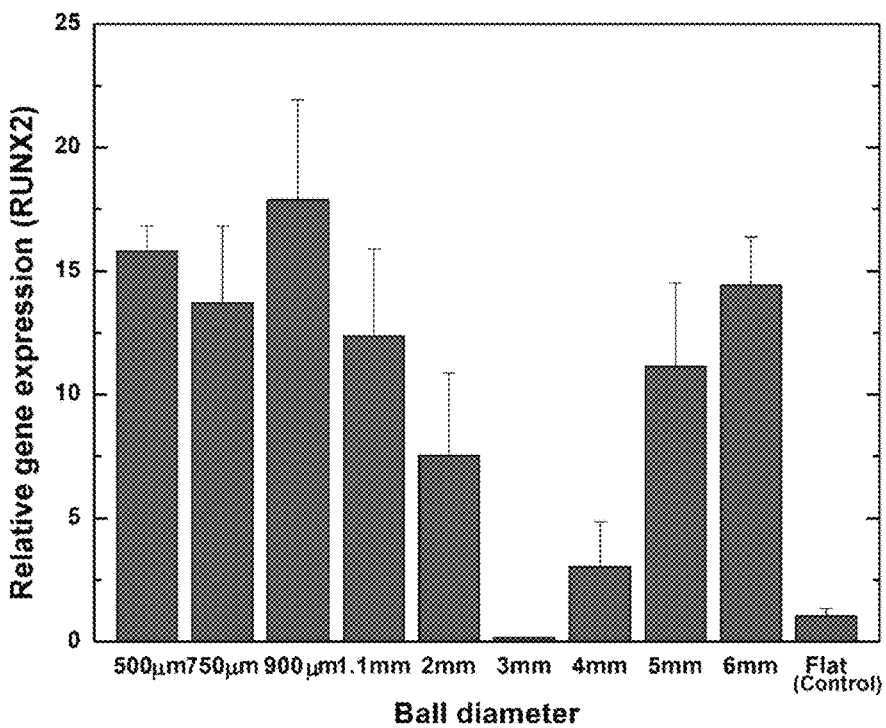
FIG. 9 shows a graph of osteogenesis induced by substrate curvatures and osteocyte differentiation induction media. Relative gene expression (RUNX2) is graphed relative to ball diameter.

According to ATCC's protocol, if the hMSCs were growing in a basal medium with growth kit only (i.e., no corresponding differentiation induction media were added to the growth media), the hMSCs growing on the flat plates should not be differentiating. The relative gene expressions of the hMSCs growing on the balls with different diameters were then computed with respect to the corresponding gene expression of the hMSCs growing on the flat plates. In FIG. 7, as shown by the expression results of the gene PPARG, an indicator of adipogenesis, the hMSCs growing on the balls with diameters of 500 µm, 750 µm, 900 µm, and 1.1 mm had significant adipogenesis after 11 days, whereas the hMSCs growing on the balls with diameters of 2 mm, 3 mm, and 4 mm, and on the flat plates had negligible adipogenesis. Therefore, the adipogenesis of the hMSCs can be induced purely by the curvatures of the substrates on which these stem cells are growing.

hMSCs were also cultured with osteocyte differentiation induction media on the micro glass ball embedded PA gels in the stem cell basal media with growth kit for 48 hours. Media was then replaced and incubated with osteocyte differentiation media for 9 days before analyzing gene expression (see FIG. 7). Results are shown in FIG. 9.

The qPCR results showed that adipogenesis can be induced purely by the substrate curvatures, i.e., the surface curvatures of the smaller glass balls. With the adipocyte differentiation induction media, the levels of the relative adipogenic gene expression are elevated for the hMSCs growing on the surfaces of the smaller glass balls. With the osteocyte differentiation induction media, the levels of the relative osteogenic gene expression of the hMSCs decreased with the decrease of the substrate ball diameter from 6 mm to 3 mm, and increased with the decrease of the substrate ball diameter from 3 mm to 500 µm.

Figure 6:
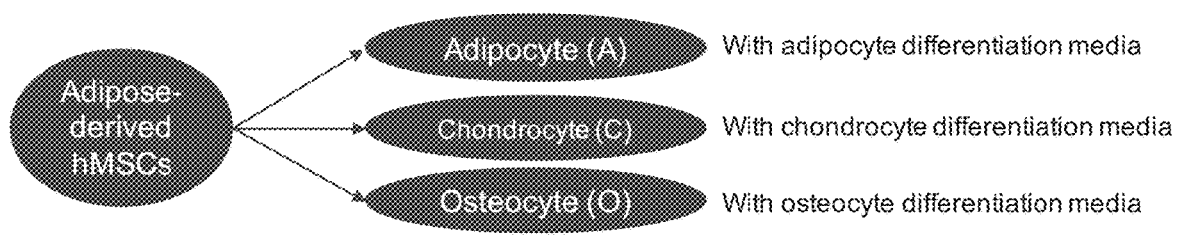
FIG. 6 illustrates differentiation responses of human adipose-derived mesenchymal stem cells (hMSCs) with various differentiation media.

In the present disclosure, hMSCs were cultured on the micro glass balls whose surfaces are curved and curvature-defined, and the spreading of the stem cells on the glass balls were natural. Since as shown in FIG. 6, the mean cell spread area of the hMSCs decreases with the decrease of the substrate ball diameter, the curvature of the substrate restricted the spreading of the hMSCs. According to the gene expression results, shown in FIG. 7, of the hMSCs growing on the balls, without the corresponding differentiation induction media, the adipogenesis of the hMSCs can be induced by the curvature of a substrate on which the stem cells are growing. This shows that curvature-alone can induce stem cell differentiation.

The cell experiments demonstrate that the class of substrates, micro glass ball embedded gels, described by this disclosure is a very useful and powerful tool for studying cell mechanobiological responses to substrate curvatures and local substrate stiffness, and for related cell and tissue engineering and biomedical applications. The related detailed and systematic studies on the effects of substrate curvatures on the differentiations of stem cells will have applications in tissue engineering and regenerative medicine, which may result in a new direction of research and development in stem cell biology and stem cell engineering/technology.

Example 2

Wrapping Over a Ball Realizes Cell Natural Isotropic-Spreading

Figure 10:
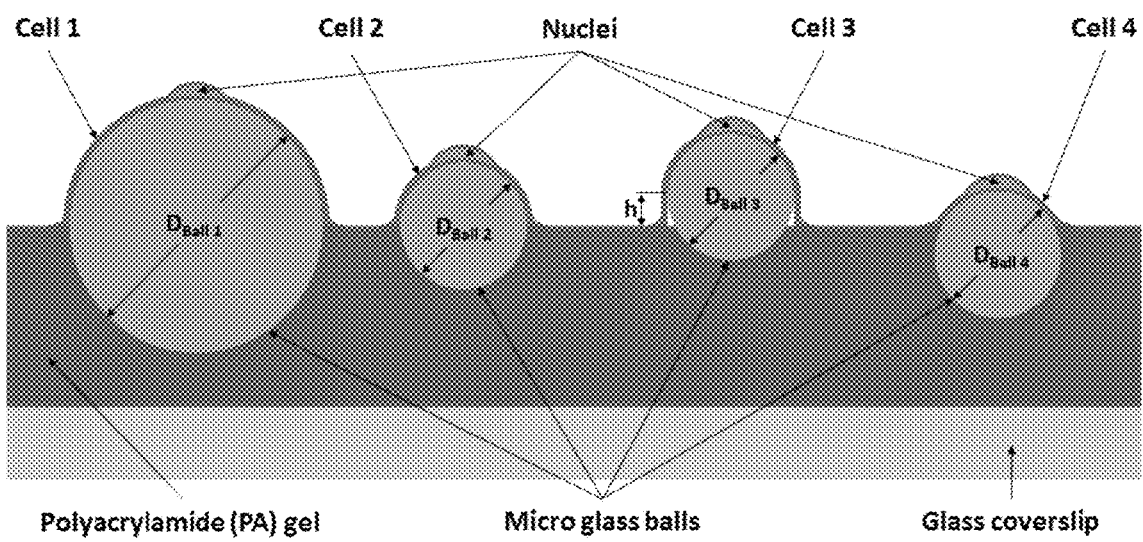
FIG. 10 shows a frontal sectional view of a schematic illustration of the different configurations of a cell wrapping over a micro glass ball embedded on the surface of a polyacrylamide (PA) gel.

FIG. 10 is a schematic illustration of the speculated different configurations of a cell wrapping over a micro glass ball embedded on the surface of a PA gel. For the configurations of Cells 1 and 2, about half of each of the embedded micro glass balls (i.e., Balls 1 and 2) is above the gel surface, and the micro glass ball (Ball 1) on which Cell 1 is growing is much larger than the micro glass ball (Ball 2) on which Cell 2 is growing. Then, the spread area of Cell 1 on the surface of Ball 1, estimated as $\pi D^2_{Ball\ 1}/2$, i.e., the half of the entire surface area of Ball 1, where $D_{Ball\ 1}$ is the diameter of Ball 1, is much larger than that of Cell 2 on the surface of Ball 2, estimated as $\pi D^2_{Ball\ 2}/2$, i.e., the half of the entire surface area of Ball 2, where $D_{Ball\ 2}$ is the diameter of Ball 2. Since Cells 1 and 2 are the same type of cells, they have similar stretching/spreading potential. Then, Cell 2 should have a much larger further spreading potential on the gel surface after wrapping over Ball 2 than Cell 1 after wrapping over Ball 1. Therefore, the relative spreading on the gel surface of Cell 2 with respect to the size of Ball 2 should be significantly larger than that of Cell 1 with respect to the size of Ball 1. But this larger should be just "significantly larger" not "much larger" because that, the Young's modulus of the glass material is about six orders of magnitude higher than that of the most rigid PA gel material used here, cells spread and migrate according to the distribution of the rigidity of a substrate (Lo et al., 2000; Discher et al., 2005), and then the spreading potential on the gel surface of the cells is much smaller than that on the glass balls. Thus, the total spread area, the spread area on the glass ball plus the spread area on the gel surface, of Cell 1 should still be much larger than that of Cell 2.

Cell 3 in FIG. 10 is growing on a micro glass ball which only has a small bottom part embedded in the gel, and this small bottom part is less than half of the entire ball. Cell 3 wrapped over the top half of the micro glass ball, extended straightly down to the gel surface, and further spread on the gel surface. Before Cell 3 reached this energetically-favorable position, it is assumed that the cell had extended and searched around to reach to and anchor on the gel surface and had rearranged its anchoring locations on the gel surface. Cell 4 in FIG. 10 is growing on a micro glass ball which only has a small top part above the gel surface (and the part of the glass ball below the gel surface is embedded in the gel), and this small top part is less than half of the entire ball. Cell 4 wrapped over this small top part of the glass ball, and further spread on the gel surface. The different configurations represented by Cells 1-4 shown in FIG. 10 should have included the possible key features of a cell wrapping over a micro glass ball embedded on the surface of a PA gel. The protocol to prepare the micro glass ball embedded PA gels was described by the authors earlier (Lee and Yang, 2012), and the Young's modulus of the PA gel was determined by the protocol of Wang and Pelham on the PA gel preparation (Wang and Pelham, 1998).

Figure 11:
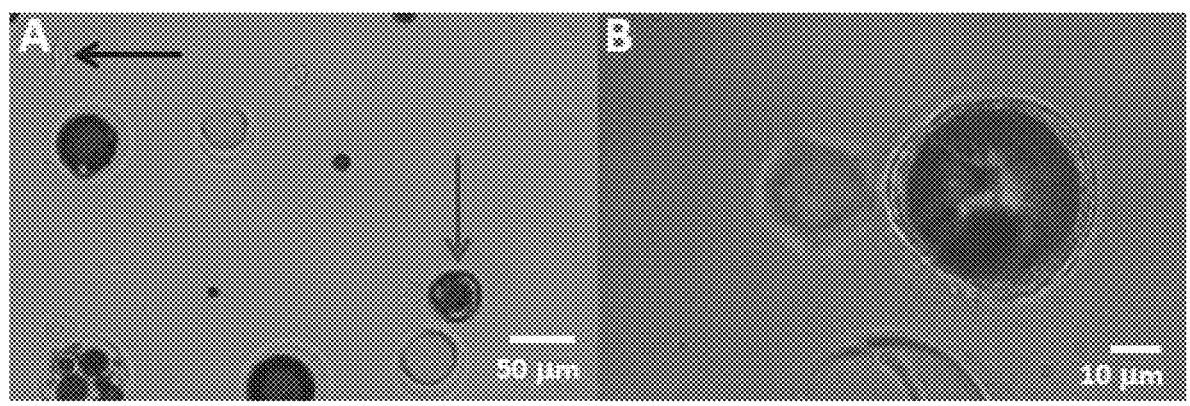
FIG. 11 shows a phase-contrast image of NIH-3T3 fibroblasts growing on a micro glass ball embedded PA gel with a Young's modulus of 75 kPa after 48 hours in culture. The left blue arrow in A (image was taken by using a 10× objective) indicates a slightly spread cell on the gel surface, and the right red arrow in A points to a cell wrapped over a micro glass ball and an enlarged view of this cell is shown in B (image was taken by using a 40× objective).
Figure 12:
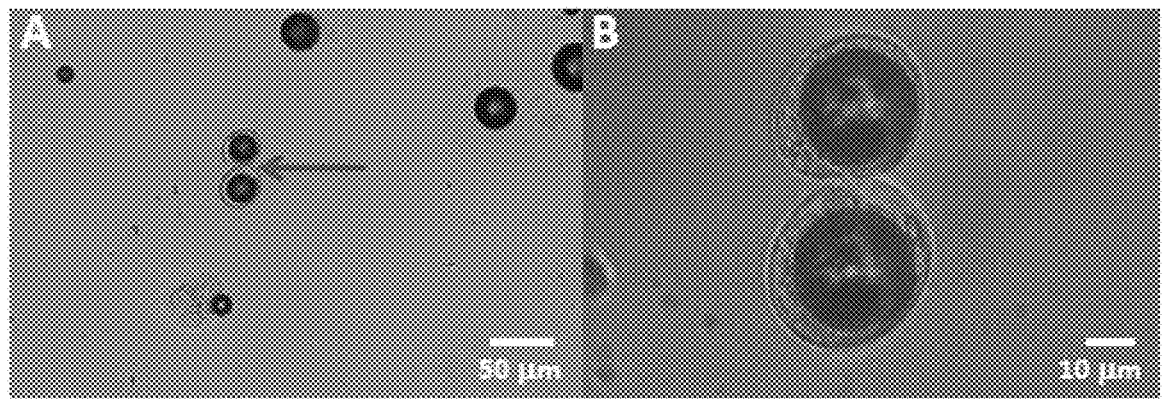
FIG. 12 shows a phase-contrast image of NIH-3T3 fibroblasts growing on a micro glass ball embedded PA gel with a Young's modulus of 10 kPa after 96 hours in culture. The red arrow in A (image was taken by using a 10× objective) points to two cells wrapped over two micro glass balls and an enlarged view of these two cells is shown in B (image was taken by using a 40× objective).
Figure 13:
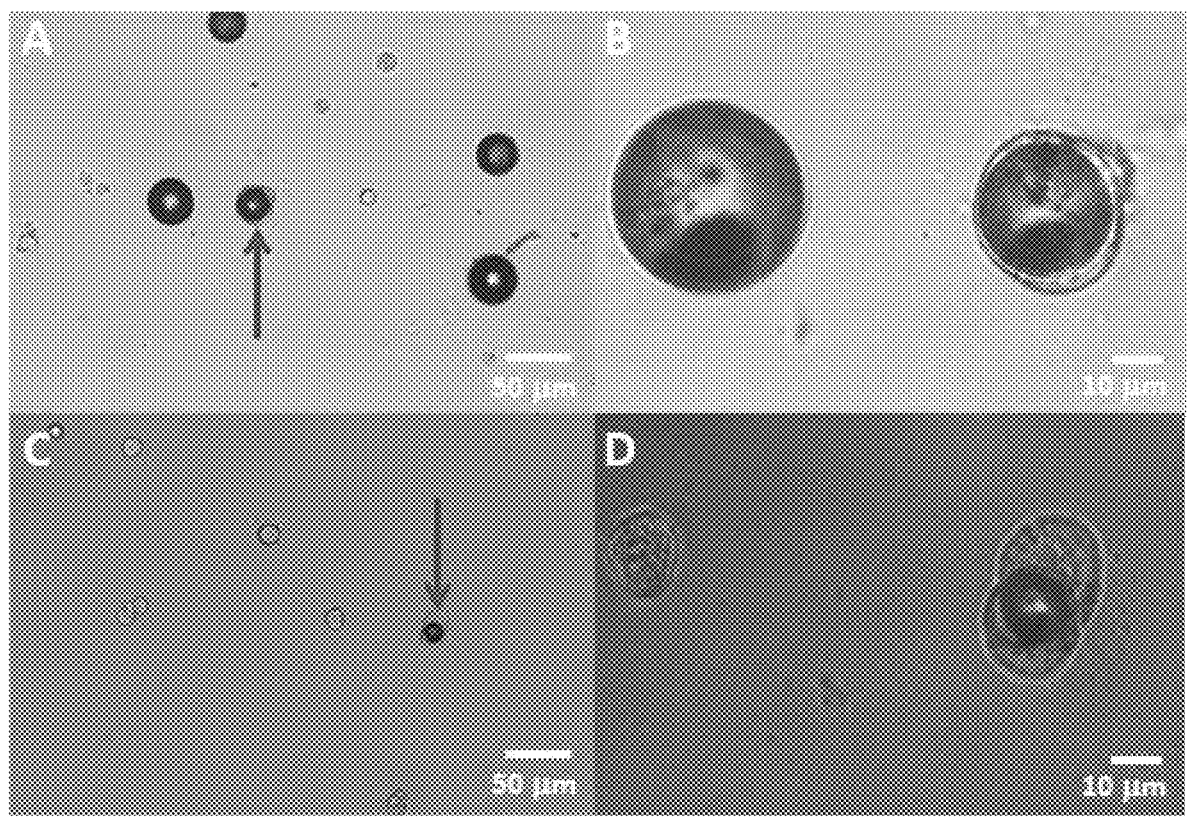
FIG. 13 shows phase-contrast images of NIH-3T3 fibroblasts growing on micro glass ball embedded PA gels with a Young's modulus of 1 kPa. The image shown in A was taken after 48 hours in culture. The red arrow in A (image was taken by using a 10× objective) points to a cell wrapped over a micro glass ball and an enlarged view of this cell is shown in B (image was taken by using a 40× objective). The image shown in C was taken after 96 hours in culture. The red arrow in C (image was taken by using a 10× objective) points to two cells wrapped over a micro glass ball and an enlarged view of these two cells is shown in D (image was taken by using a 40× objective).

FIGS. 11-13 show the phase-contrast images of the NIH-3T3 fibroblasts growing on the micro glass ball embedded PA gels with Young's moduli of 75 kPa, 10 kPa, and 1 kPa, respectively. It can be seen that some cells, indicated by the red arrows, wrapped over the micro glass balls and reached the gel surfaces, and further spread on the gel surfaces. Because of the imaging nature of the phase-contrast images and because the PA gels are transparent, based on a phase-contrast image we cannot determine the part of an embedded micro glass ball that is above the gel surface and the part of the embedded ball that is below the gel surface. But this does not influence the authors to achieve the objective of this research, to identify the effect of wrapping over a ball on the spreading morphology of a cell, which can be accomplished by analyzing the obtained phase-contrast images. Irrespective of the different diameters of the micro glass balls, different elasticities (i.e., different Young's moduli) of the PA gels, and different relative locations of the micro glass balls with respect to the geometric centers of the fibroblasts, the spreading morphologies of the fibroblasts wrapping over the micro glass balls in FIGS. 11-13 showed a common characteristic: the outlines or boundaries of these fibroblasts were roughly circular and smooth, and had no obvious angles, corners, and straight edges. This roughly-circular and smooth characteristic of the outlines or boundaries of these fibroblasts indicated that, these fibroblasts were in isotropic-spreading, and for each of these fibroblasts the extent of the cell spreading in every direction is roughly the same from the geometric center of the fibroblast.

Because of the geometrically-isotropic nature of the surface of a ball, the isotropic-spreading cell morphologies observed here were formed by wrapping over the micro glass balls, and these cells naturally isotropically spread over the balls and further naturally spread on the adjacent gel surfaces. Therefore, the cell isotropic-spreading observed here is cell natural isotropic-spreading, and this is in contrast to the cell isotropic-spreading observed by culturing cells on the geometric patterns or chemical patterns to control or restrict the spreading of the cells. The readers can appreciate the characteristics and uniqueness of the cell natural isotropic-spreading observed here by recalling the irregular and non-uniform nature of the normal cell natural spreading observed in the culture dishes, on the flat glass slides (Alberts et al., 2015; ATCC, VA; Life Technologies Corp., N.Y.), on the flat gels (Lo et al., 2000; Discher et al., 2005; Engler et al., 2006), on the glass balls but without wrapping over the balls (Lee and Yang, 2012), on the glass fibers (Lee and Yang, 2012; Dunn and Heath, 1976), and on the PLGA microfibers (Hwang et al., 2009), where the extent of the cell spreading in each direction and the resulting cell outline or boundary were random, and the cell spreading morphologies had sharp angles, corners, and straight edges. In summary, FIGS. 11-13 showed that wrapping over a ball realizes cell natural isotropic-spreading. The rough quantitative estimations of the cell spread areas and their comparisons of the fibroblasts (shown in FIGS. 11-13) wrapping over the micro glass balls are presented in the following.

Example 3

Estimating the Spread Area of a Cell that Wrapping Over a Ball

The spread area of a cell that wrapped over a ball and further spread on the adjacent gel surface is roughly estimated as the spread area of the cell on the ball plus the spread area of the cell on the gel surface. The spread area of the cell on the ball is roughly estimated as $\pi D^2_{Ball}/2$, i.e., the surface area of the top half of the ball, where $D_{Ball}$ is the diameter of the ball. According to the configurations of the Cells 1-4 in FIG. 10, this estimation of the spread area of the cell on the ball, $\pi D^2_{Ball}/2$, is the upper bound of the spread area of the cell on the ball, and as described in the above for FIG. 10, it is an accurate estimation for the Cells 1-3, but it is an overestimate for the Cell 4 since the surface area of the ball covered by the Cell 4 is smaller than half of the ball. The spread area of the cell on the gel surface is roughly estimated as the projected area of the cell onto the flat gel surface minus $\pi D^2_{Ball}/4$, i.e., minus the area of the diametrical circle of the ball. Again obviously, this estimation of the spread area of the cell on the gel surface is an accurate estimation for the Cells 1-3, but is an underestimate for the Cell 4. The estimated total spread area of a cell, the spread area of the cell on the ball plus the spread area of the cell on the gel surface, is an accurate estimation for the Cells 1 and 2, but is an underestimate for the Cell 3 since the spread area of the cell between the part of the cell that attached to the ball and the part of the cell that attached to the gel surface, i.e., the area of the vertical part of the cell morphology which is cylindrical and equal to $\pi D_{Ball} h$ where h is the distance between the part of the cell that attached to the ball and the part of the cell that attached to the gel surface, is not included. For the Cell 4, this estimated total spread area of the cell is an overestimate because the overestimate in the estimation of the spread area of the cell on the ball is greater than the underestimate in the estimation of the spread area of the cell on the gel surface.

As mentioned in the above, based on a phase-contrast image shown in FIGS. 11-13, one cannot determine the relative height between the embedded micro glass ball and the gel surface. However, the following three reasons support the assumption that the fibroblasts wrapping over the micro glass balls shown in FIGS. 11-13 initially belonged to the configurations represented by Cells 1-3 shown in FIG. 10, i.e., about half or more than half of each of the embedded micro glass balls was above the corresponding gel surface, and if a fibroblast wrapping over a micro glass ball shown in FIGS. 11-13 belonged to the configuration represented by Cell 3 shown in FIG. 10, the vertical distance from the geometric center of the micro glass ball to the gel surface should be much smaller than the radius of the micro glass ball, i.e., the geometric center of the micro glass ball was a little above the gel surface or a little smaller than half of the micro glass ball was under the gel surface. First, as shown in the scanning electron microscope (SEM) image (not shown here) of a micro glass ball embedded PA gel published by the authors earlier (Lee and Yang, 2012), about half or more than half of each of the embedded micro glass balls was above the gel surface. Secondly, the micro glass balls used to make the micro glass ball embedded PA gels were not solid balls, they were empty balls, or they were made of glass shells. Thus they were lighter than the PA solutions, and they were floating on the top of the PA solutions. The authors had to use coverslips to press the micro glass balls down into the PA solutions to make the micro glass ball embedded PA gels. During and after the polymerization process of the PA solutions, because of the lighter situation, the micro glass balls were believed to move gradually upward in the polymerizing PA solutions and polymerized PA gels to reach a force equilibrium in the vertical direction. When the prepared micro glass ball embedded PA gels were used for cell culturing, the experiences of the authors told the authors that about half or more than half of each of the embedded micro glass balls on which there were fibroblasts growing should be above the gel surface and if it was the case that more than half of an embedded micro glass ball on which there were fibroblasts growing was above the gel surface, the geometric center of the micro glass ball was just a little above the gel surface. Thirdly, for an embedded micro glass ball to survive (i.e., not detach from the gel during) the entire handling (including transportation, rinsing, and adding the cell culture media) process, for an embedded micro glass ball to provide a stable substrate for a cell to adhere and spread, and for an embedded micro glass ball to survive the entire cell growing process until the imaging time, about half or a little smaller than half of the micro glass ball need to be under the gel surface.

The stabilized configurations (or can be called the final configurations in contrast to the initial configurations mentioned at the beginning of last paragraph) of the fibroblasts wrapping over the micro glass balls shown in FIGS. 11-13 should only belong to the configurations represented by Cells 1 and 2 shown in FIG. 10, i.e., about half of each of the embedded micro glass balls was above the corresponding gel surface. This is because the vertical adhesion/pulling forces between the cell and the gel surface will gradually press the micro glass ball down a little and pull the gel surface up a little to adjust the vertical relative position between the cell and the gel surface to reach an optimum mechanobiologically-comfortable position/morphology of the cell, and Cell 3 in FIG. 10 has a vertically-stretched (with a height of h) part and was not believed to be a mechanobiologically-comfortable position and a cell should prefer the position of Cell 1 or 2 more than the position of Cell 3 in FIG. 10. Due to the relatively very large volume of the gel material surrounding the embedded micro glass ball, the vertical deformation induced by the vertical adhesion/pulling forces between the cell and the gel surface will not significantly change the planar nature of the gel surface. One additional justification of the above statement, the stabilized configurations of the fibroblasts wrapping over the micro glass balls shown in FIGS. 11-13 should only belong to the configurations represented by Cells 1 and 2 in FIG. 10, was that, the part of the morphology of each of these fibroblasts on the corresponding PA gel surface indicated that the fibroblast wrapped over approximately the top half of the micro glass ball and there was no obvious vertically-stretched part, otherwise if the fibroblasts had the configurations represented by Cells 3 and 4 in FIG. 10, the fibroblasts would have not spread such uniformly around the diameters of the balls. Therefore, for the fibroblasts wrapping over the micro glass balls shown in FIGS. 11-13, the method introduced in the first paragraph of this section should give reasonably-accurate estimations for the spread area of a fibroblast on the ball, for the spread area of this cell on the gel surface, and for the total spread area of this cell.

In FIG. 11, the fibroblast wrapped over a micro glass ball (embedded in a PA gel with a Young's modulus of 75 kPa) with a diameter of 33.8 µm, and the image was taken after 48 h in culture. The spread area of this cell on the ball was estimated as 1794.5 µm$^2$ and the spread area of this cell on the gel surface was estimated as 421.4 µm$^2$. The total spread area of this cell was then estimated as 2215.9 µm$^2$. The projected area of this cell onto the flat gel surface was measured as 1318.6 µm$^2$. In the below, the projected area of a cell onto a flat gel surface is called the cell projected area or the projected area of this cell. Since as stated in the above, the morphologies of the observed fibroblasts wrapping over the micro glass balls were approximately circular, the diameter of such a fibroblast was estimated according to the following areal relation, cell projected area=$\pi D_{cell}^2/4$, where Dun was the estimated diameter of this fibroblast. The diameter of the fibroblast wrapping over the micro glass ball in FIG. 11 was then estimated as 41.0 µm, which was 1.213 times the diameter of the micro glass ball, i.e., the further spreading of this cell on the gel surface in the radial direction (after this cell wrapped over the micro glass ball) was approximately 21.3% of the radius of the micro glass ball.

In FIG. 12, there are two fibroblasts wrapped over the two micro glass balls (embedded in a PA gel with a Young's modulus of 10 kPa). The upper fibroblast in FIG. 12 (B) wrapped over a micro glass ball with a diameter of 24.4 µm. The spread area on the ball, the spread area on the gel surface, and the total spread area of this cell were estimated as 935.2, 303.7, and 1238.9 µm², respectively. The projected area of this cell was measured as 771.3 µm², and the diameter of this cell was estimated as 31.3 µm which was 1.283 times the diameter of the micro glass ball, i.e., the further spreading of this cell on the gel surface in the radial direction was approximately 28.3% of the radius of the micro glass ball. The lower fibroblast in FIG. 12 (B) wrapped over a micro glass ball with a diameter of 25.2 µm. The spread area on the ball, the spread area on the gel surface, and the total spread area of this cell were estimated as 997.5, 416.5, and 1414.0 µm², respectively. The projected area of this cell was measured as 915.2 µm², and the diameter of this cell was estimated as 34.1 µm which was 1.353 times the diameter of the micro glass ball, i.e., the further spreading of this cell on the gel surface in the radial direction was approximately 35.3% of the radius of the micro glass ball. Since the image shown in FIG. 12 was taken after 96 h in culture, these two cells (the just mentioned upper fibroblast and lower fibroblast in FIG. 12 (B)) may be the two daughter cells of a cell division. Compared with the situation of the fibroblast wrapped over the micro glass ball in FIG. 11, the two micro glass balls in FIG. 12 were much smaller, and then the cell spread areas on the micro glass balls of the two fibroblasts in FIG. 12 were much smaller than that of the fibroblast in FIG. 11. But the relative (with respect to the radius of the micro glass ball) further spreading in the radial direction of these two fibroblasts on the gel surface were significantly larger than that of the fibroblast in FIG. 11 even though the PA gel in FIG. 12 was much softer than the PA gel in FIG. 11, which indicated that these two fibroblasts tended to spread more on the gel surface because they spread less on the micro glass balls. This observation agreed well with the theoretical reasoning presented in the above in the description of FIG. 10 for the configurations of Cells 1 and 2.

In FIG. 13, the micro glass balls were embedded in a PA gel with a Young's modulus of 1 kPa. The images shown in FIGS. 13 (A) and (B) were taken after 48 hours in culture, and the fibroblast in FIG. 13 (B) wrapped over a micro glass ball with a diameter of 26.5 µm. The images shown in FIGS. 13 (C) and (D) were taken after 96 hours in culture, and in FIG. 13 (D) the two fibroblasts wrapped over the micro glass ball may be the two daughter cells of a cell division. In FIG. 13 (D) the micro glass ball has a diameter of 15.2 µm, which was much smaller than that of the micro glass ball wrapped over by the fibroblast in FIG. 13 (B). Therefore, the situations that FIG. 13 intended to observe combined the situations that were observed in FIGS. 11 and 12, but here in FIG. 13 the micro glass balls in both FIGS. 13 (A) and (B) and FIGS. 13 (C) and (D) were embedded in a PA gel with a Young's modulus of 1 kPa, whereas in FIGS. 11 and 12 the micro glass balls were embedded in PA gels with Young's moduli of 75 and 10 kPa, respectively. For the fibroblast in FIG. 13 (B) wrapped over the micro glass ball, the spread area on the ball, the spread area on the gel surface, and the total spread area of this cell were estimated as 1103.1, 190.3, and 1293.4 µm², respectively. The projected area of this cell was measured as 741.8 µm², and the diameter of this cell was estimated as 30.7 µm which was 1.158 times the diameter of the micro glass ball, i.e., the further spreading of this cell on the gel surface in the radial direction was approximately 15.8% of the radius of the micro glass ball.

For the upper one of the two fibroblasts wrapped over the micro glass ball in FIG. 13 (D), the spread area on the ball, the spread area on the gel surface, and the total spread area of this cell were estimated as 362.9, 160.6, and 523.5 µm², respectively. The projected area of this cell was measured as 342.0 µm², and the diameter of this cell was estimated as 20.9 µm which was 1.375 times the diameter of the micro glass ball, i.e., the further spreading of this cell on the gel surface in the radial direction was approximately 37.5% of the radius of the micro glass ball. For the lower one of the two fibroblasts wrapped over the micro glass ball in FIG. 13 (D), the spread area on the ball, the spread area on the gel surface, and the total spread area of this cell were estimated as 362.9, 121.8, and 484.7 µm², respectively. The projected area of this cell was measured as 303.2 µm², and the diameter of this cell was estimated as 19.6 µm which was 1.289 times the diameter of the micro glass ball, i.e., the further spreading of this cell on the gel surface in the radial direction was approximately 28.9% of the radius of the micro glass ball. Compared with the situation in FIG. 13 (B), the micro glass ball in FIG. 13 (D) was much smaller, and then the cell spread areas on the micro glass ball of the two fibroblasts in FIG. 13 (D) were much smaller than that of the fibroblast in FIG. 13 (B). But the relative further spreading in the radial direction of these two fibroblasts on the gel surface were significantly larger than that of the fibroblast in FIG. 13 (B), which indicated that these two fibroblasts tended to spread more on the gel surface because they spread less on the micro glass ball. This observation again agreed well with the theoretical reasoning presented in the above in the description of FIG. 10 for the configurations of Cells 1 and 2. Moreover, the relative further spreading in the radial direction of the fibroblast in FIG. 13 (B) on the gel surface was significantly smaller than those of the fibroblasts in FIGS. 11 and 12, and this may be due to the fact that the PA gel in FIG. 13 was much softer than the PA gels in FIGS. 11 and 12. But since the micro glass ball in FIG. 13 (D) was too small, the cell spread areas on the micro glass ball of the two fibroblasts (the just mentioned upper fibroblast and lower fibroblast in FIG. 13 (D)) in FIG. 13 (D) were also too small. The relative further spreadings in the radial direction of these two fibroblasts on the gel surface were still similar to those of the two fibroblasts in FIG. 12 (B), which again supported the above-mentioned notion that these two fibroblasts tended to spread more on the gel surface because they spread less on the micro glass ball.

Example 4

Mechanism for the Observed Cell Natural Isotropic-Spreading

The attachment rate and spreading morphology of the NIH-3T3 fibroblasts are sensitive to the diameters of their substrate micro glass balls, i.e., are sensitive to the curvatures of their substrates (Lee and Yang, 2012). For the fibroblasts growing on the micro glass balls with diameters of 500 µm and below, round shapes were the dominant cell morphology, and some cells made one or two long and narrow lamellipodia while the cell body was still round. These indicated that the large curvatures of the surfaces of small micro glass balls, such as the micro glass balls with diameters of 500 µm and below, inhibit the formation of long stress fibers inside a cell.

Figure 14:
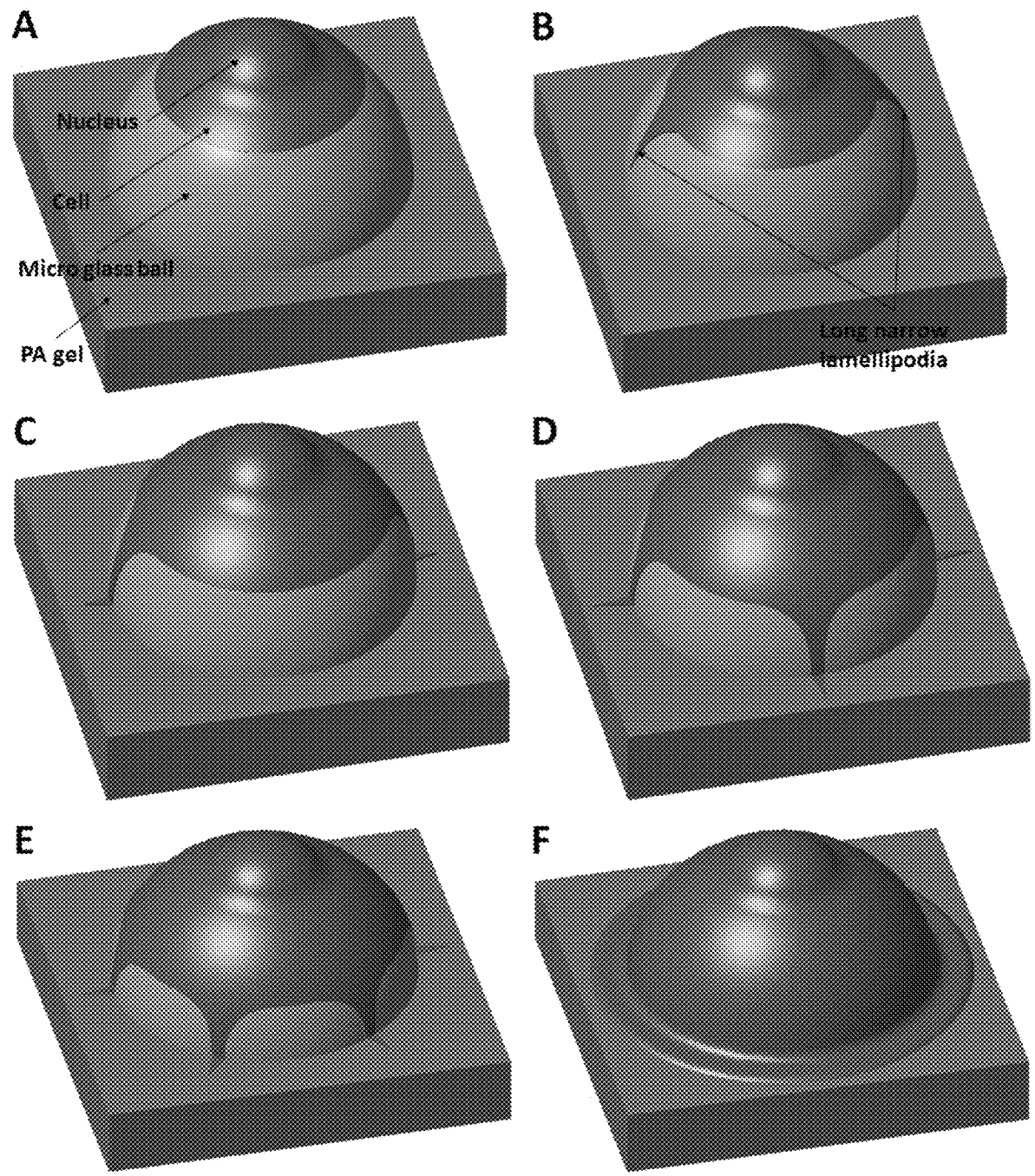
FIG. 14 shows a three-dimensional (3-D) schematic drawing to show the speculated mechanism or process to form the observed cell natural isotropic-spreading here, i.e., the speculated process for a cell to wrap over a micro glass ball.

FIG. 14 schematically shows the mechanism or process to form the observed cell natural isotropic-spreading here, i.e., the speculated process for a cell to wrap over a micro glass ball. In FIG. 14 (A), a cell attached to a micro ball and started to spread. Because of the large surface curvature of the micro ball, long stress fibers inside the cell could not be formed, and then the cell made two long and narrow lamellipodia in two opposite or symmetric and energetically-favorable directions while the cell body was still round (FIG. 14 (B)). The symmetric distribution of these two long and narrow lamellipodia with respect to the cell body was to ensure the statical equilibrium of the cell. Because of the small size of the micro ball, the two long and narrow lamellipodia could extend to reach to the surface of the gel, and formed focal adhesions with the gel surface (FIG. 14 (C)). The adhesion forces provided by these two adhesion sites, formed between the two long and narrow lamellipodia and the gel surface, made the cell more stretched and spreading morphology more stable. This more stabilized cell morphology provided the cell with more freedom to spread, and then the other two opposite or symmetric and energetically-favorable sites on the periphery of the round part of the cell body started to extend to make long and narrow lamellipodia, and these two newly-made long and narrow lamellipodia could also extend to reach to the surface of the gel, and formed focal adhesions with the gel surface (FIG. 14 (D)). This process continued at the other sites on the periphery of the round part of the cell body (FIG. 14 (E)) until the entire cell periphery extended and adhered to the gel surface (FIG. 14 (F)). The cell periphery further naturally spread on the adjacent gel surface and this further spreading was roughly-isotropic because of the lack of long stress fibers inside the cell. Therefore, in short, the underlying reason for the cell natural isotropic-spreading observed here was speculated as follows: The large curvature of the surface of a ball inhibits the formation of long stress fibers inside a cell, and the adhesion forces between the cell and the adjacent gel surface pull the cell to spread to wrap over the ball and further spread on the adjacent gel surface roughly in the same amount in every direction.

Example 5

Micro Glass Ball Embedded PA Gel Experimental Platforms

Figure 15:
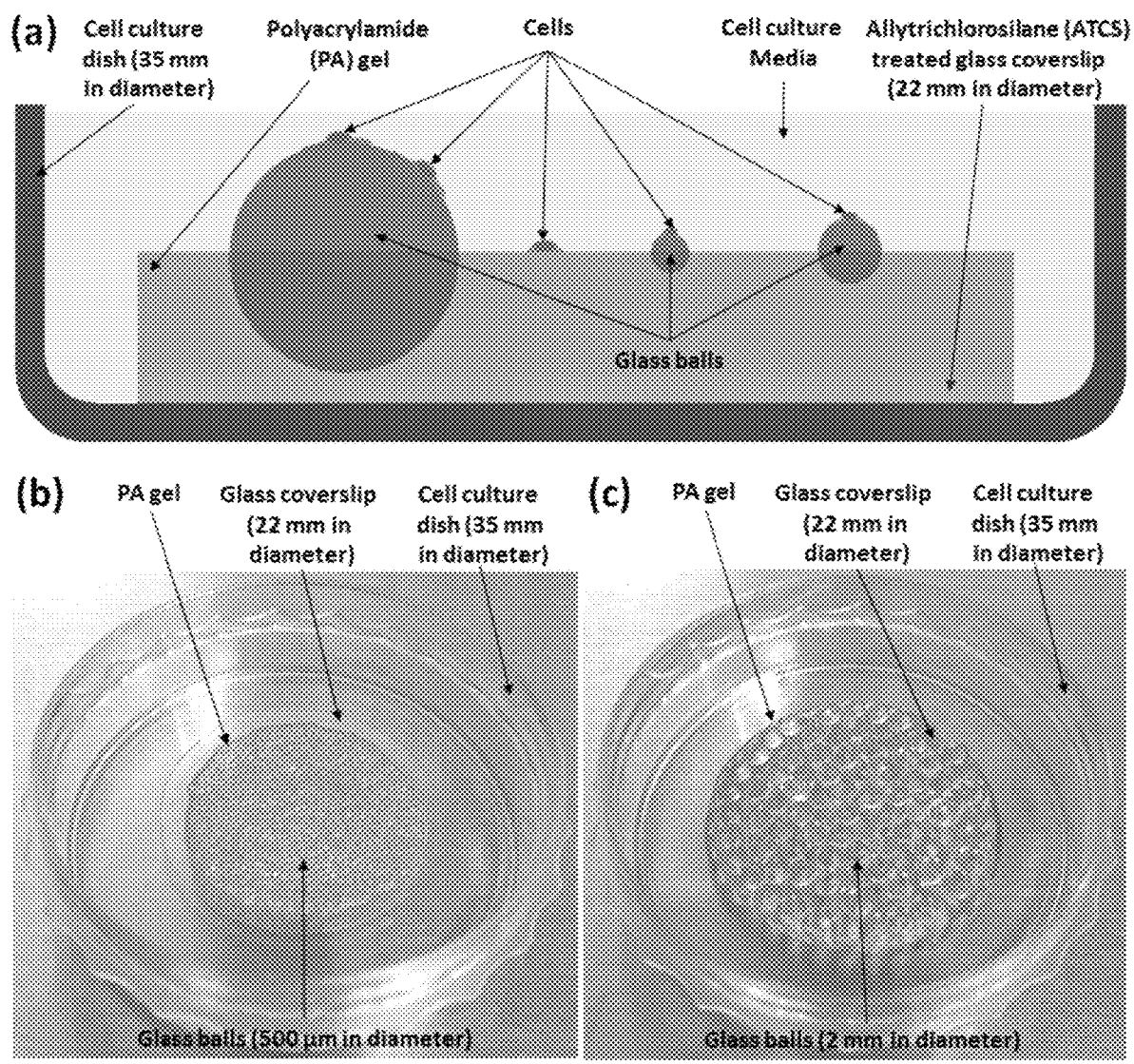
FIG. 15 shows micro glass ball embedded PA gel experimental platforms providing unique and powerful 3-D micromechanical environments to study cell mechanobiological responses to substrate curvatures and local substrate stiffness. (a) Schematic drawing of a platform. (b)-(c) Brightfield optical pictures of two experimental platforms with embedded glass balls having diameters of 500 μm and 2 mm, respectively.

A class of PA gels embedded with micro glass balls having diameters of mixed 5-100 µm, mixed 50-300 µm, 500 µm, 750 µm, 900 µm, 1.1 mm, 2 mm, 3 mm, and 4 mm were prepared by using the protocol described in Materials and Methods. FIG. 15 (a) shows the schematic drawing of a micro glass ball embedded PA gel experimental platform for studying cell mechanobiological responses to substrate curvatures. Since this platform is non-flat, it provides a 3D micromechanical environment for cell culturing. Also, since the surface curvatures of the non-flat glass balls are known or defined, we say this 3D micromechanical environment is curvature-defined. In this platform, the polymerized PA gel is to fix the glass balls at certain locations on and to prevent any rolling and detaching of the glass balls from the gel surface. FIGS. 15 (b) and (c) show bright-field optical pictures of two PA gel experimental platforms with embedded glass balls having diameters of 500 µm and 2 mm, respectively.

Example 6

Effects of Substrate Curvatures on the Spreading of NIH-3T3 Fibroblasts

The surface curvature of a substrate is the reciprocal of the radius of the substrate. Among the used diameters of glass balls, it was found that the minimum diameter of a glass ball on which a NIH-3T3 fibroblast can attach and spread without wrapping over the ball was 58 µm. A fibroblast wrapping over a ball means this fibroblast covered the entire upper exposed portion of the embedded ball in a PA gel and further spread on the adjacent gel surface. The cell attachment rate is defined as the ratio between the number of the attached and spread cells on the glass balls and the number of the seeded cells in a cell culture dish. The cell attachment rates were not quantitatively measured, and the cell attachment rates were difficult to measure because the number of the attached and spread cells on the glass balls was difficult to count. As shown in FIGS. 15 (b) and (c), the embedded glass balls were packed on the surfaces of the PA gels. Since we seeded the same number of cells into each cell culture dish, we used the chance of finding an attached and spread cell on a glass ball as a qualitative measure of the cell attachment rate on the glass balls with a same diameter and packed on the surface of a PA gel, and then we qualitatively found that the cell attachment rate of the fibroblasts decreased with the decrease of the substrate ball diameter.

Figure 16:
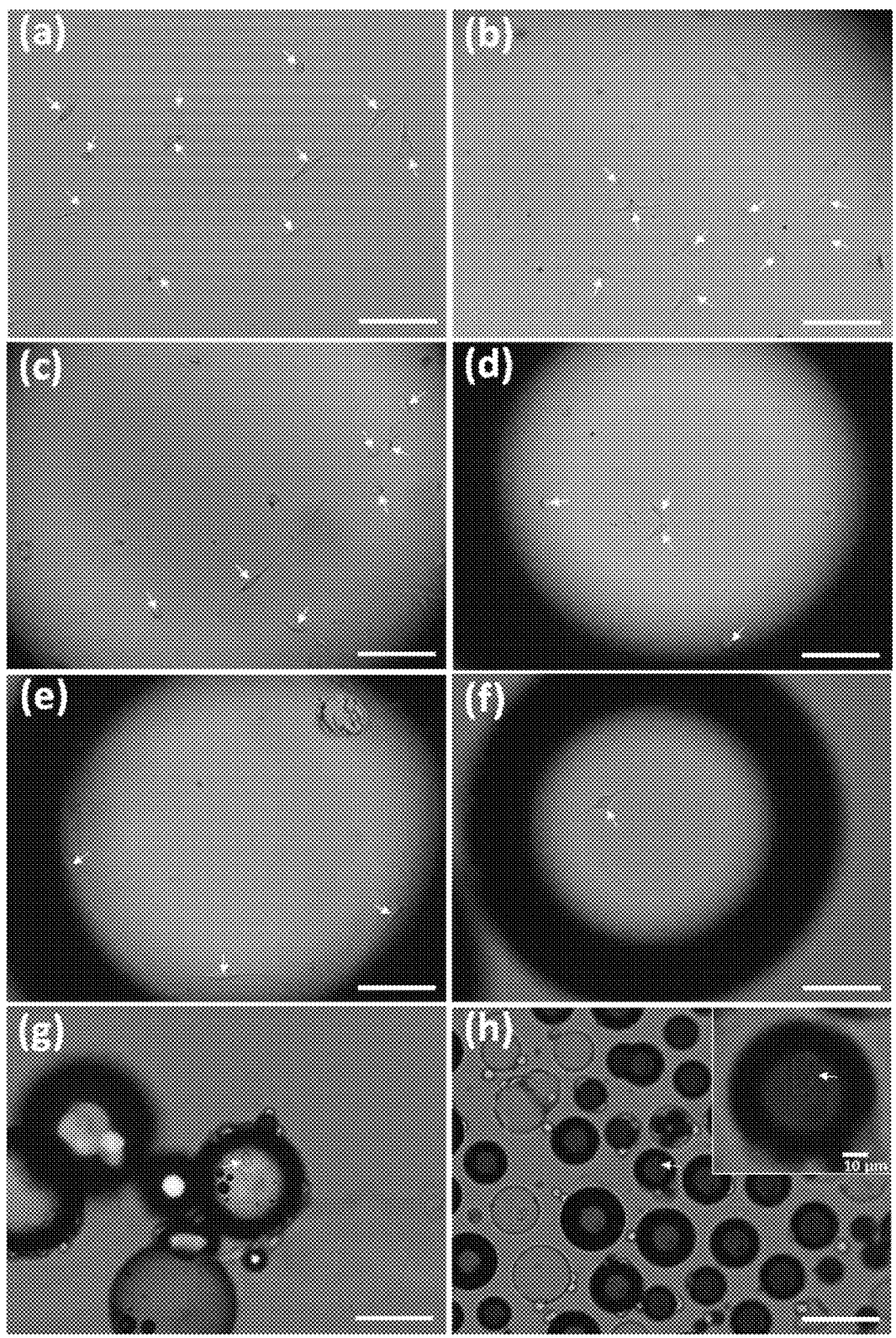
FIG. 16 shows effects of substrate curvatures on the spreading morphologies of the NIH-3T3 fibroblasts. As is known, the surface curvature of a substrate is the reciprocal of the radius of the substrate. The fibroblasts were plated on the PA gels embedded with micro glass balls having diameters from 5 μm to 2 mm, and the phase-contrast images were taken after 24 hours in culture. Fibroblasts growing on a flat glass plate (22 mm-square glass coverslip) (a), and on a 2 mm-(b), 1.1 mm-(c), 900 μm-(d), 750 μm-(e), 500 μm-(f), 147 μm-(g), and 58 μm-(h) diameter glass ball are indicated by the white arrows. Scale bars (except the one in the inset of (h)): 100 μm.

FIG. 16 shows the effects of the substrate curvatures on the spreading morphologies of the NIH-3T3 fibroblasts growing on the micro glass balls with various diameters. The following morphological observations on the fibroblasts growing on the micro glass balls with various diameters were reported (Lee and Yang, 2012; incorporated herein by reference in entirety). But in FIG. 2 of Lee and Yang, the phase-contrast images of the fibroblasts growing on the glass balls were taken by using a 40× objective to show the morphology of a single cell, while here in FIG. 16, the phase-contrast images were taken by using a 10× objective to cover much larger surface areas of the glass balls to show the morphologies of multiple cells growing on a glass ball. Therefore, one can learn the following information from FIG. 16 here, the zoom-out view of a cell growing on a ball surface and the morphologies of different cells growing on the same ball surface. The present disclosure describes the effects of the substrate curvatures on the spreading morphologies of the fibroblasts.

In the experiments, it was observed that after 24 hours in culture, the NIH-3T3 fibroblasts started to divide and the two daughters of an original cell were connected to each other. Therefore, to image single fibroblasts, 24 hours in culture was chosen as the fibroblasts' imaging time. After 24 hours in culture, the fibroblasts growing on the flat glass plate (FIG. 16 (a)) were well-spread, and the spreading morphologies of these fibroblasts were almost indistinguishable from those of the fibroblasts growing on the 2 mm-diameter glass ball (for brevity, the words "growing", "diameter", and "glass" in this statement will be omitted in the below in the same or similar statements unless this omission may induce unclarity, e.g., this statement will read as "fibroblasts on the 2 mm-ball" and "the flat glass plate(s)"

will read as "the flat plate(s)" in the below) (FIG. 16 (b)). Both the fibroblasts on the flat plate and the fibroblasts on the 2 mm-ball had two or three lamellipodia for active migration. Although both the fibroblasts on the 2 mm ball and the fibroblasts on the flat plate had the similar morphologies and behaviors, the fibroblasts on the 2 mm-ball were slightly less spread than the fibroblasts on the flat plate. This means that these cells can sense the small substrate curvature of a large substrate radius or diameter, such as the small surface curvature of the 2 mm-diameter substrate glass balls used herein.

Compared with the fibroblasts on the flat plate and 2 mm-ball, the fibroblasts on the 1.1 mm-(FIG. 16 (c)), 900 μm-FIG. 16 (d)), and 750 μm-(FIG. 16 (e)) balls were less spread and had the similar morphologies which are different from those of the fibroblasts on the flat plate and 2 mm-ball. While some of the fibroblasts on the 1.1 mm-, 900 μm-, and 750 μm-balls had the round shapes with two short and wide lamellipodia after 24 hours in culture, the majority of the fibroblasts had the more spread shapes.

The fibroblasts on the balls with diameters of 500 μm and below (FIGS. 16 (f), (g), and (h)) had the very different cell shapes, compared with those on the larger balls. For these cells, the round shapes were the dominant cell morphology, and some of the cells made one or two long and narrow lamellipodia while the cell body was still round. As shown in FIGS. 16 (g) and (h), the morphologies of the fibroblasts on the 147 μm- and 58 μm-balls closely resembled the morphology of the fibroblast on the 500 μm-ball (FIG. 16 (f)), and all the three fibroblasts were round with one or two lamellipodia. It was also observed that the fibroblasts on the balls with diameters of 500 μm and below did not spread and migrate actively, and they grew minimally and remained round after 48 hours in culture.

For the cells growing on the balls, the cell dimensions, including the cell lengths and widths, and the cell spread areas are all important quantitative information to reveal the effects of the substrate curvatures on cell shape and function. Then, the cell lengths, cell widths, and cell spread areas were measured for a number of randomly-selected fibroblasts growing on the flat plates and on the balls. For the fibroblasts growing on the flat plates, 10 cells were measured, and for the fibroblasts growing on the 2 mm-, 1.1 mm-, 900 μm-, 750 μm-, and 500 μm-balls, 10 cells were measured for each ball diameter. For the fibroblasts growing on the balls with diameters of 300 μm and below, since the cell attachment rates of these balls were much lower than those of the balls with diameters of 500 μm and above, 35 cells in total were measured, including the cell on a ball with a diameter of 58 μm (as mentioned in the above, 58 μm was the observed minimum diameter of a glass ball on which a fibroblast can attach and spread without wrapping over the ball). Then the total number of the measured fibroblasts is $n_{fibroblasts}=10\times(1+5)+35=95$.

Figure 17:
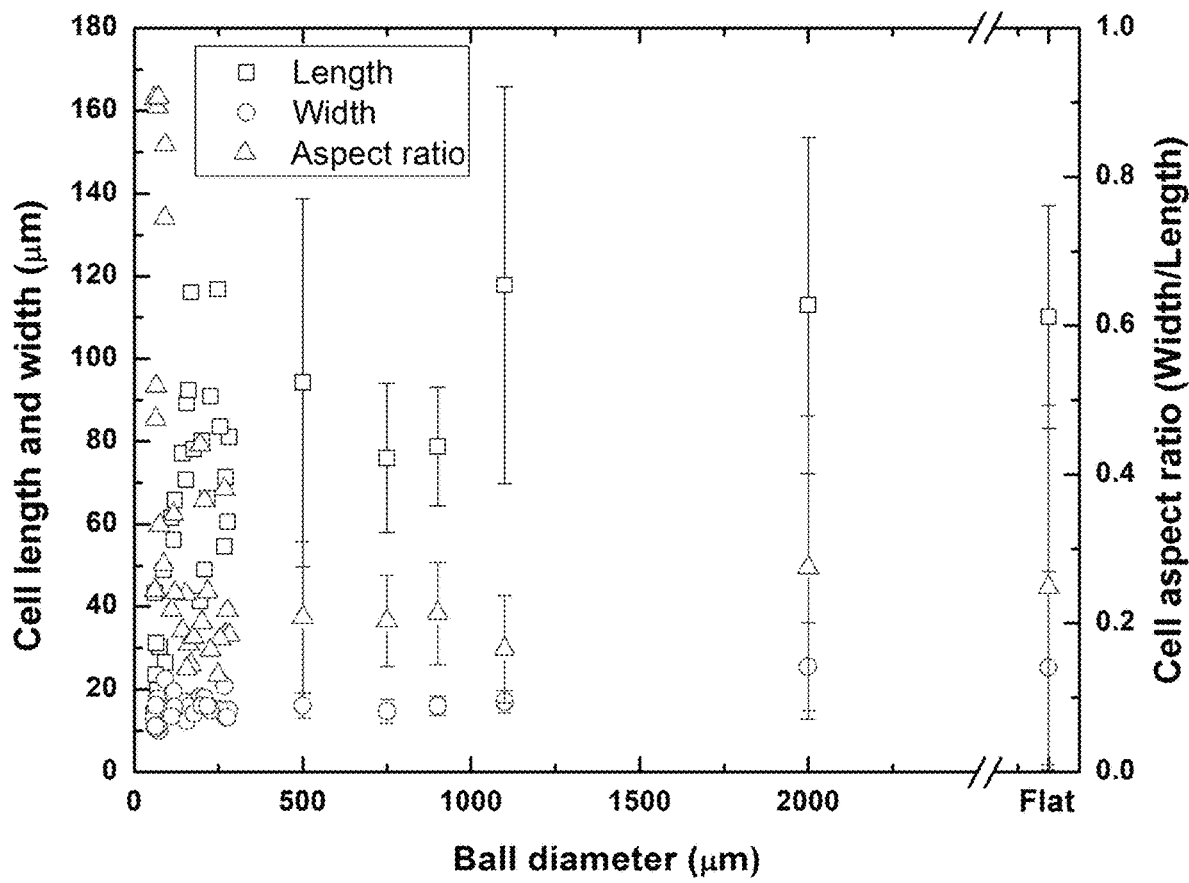
FIG. 17 shows cell length and width versus ball diameter for the NIH-3T3 fibroblasts. The cell lengths and widths were measured for a number of randomly-selected cells ($n_{fibroblasts}$=95) growing on the flat glass plates and on the glass balls. For the fibroblasts growing on the flat glass plates, 10 cells were measured, and for the fibroblasts growing on the 2 mm-, 1.1 mm-, 900 μm-, 750 μm-, and 500 μm-diameter glass balls, 10 cells were measured for each ball diameter, and the results shown are mean±standard deviation (SD) for each ball diameter including the case of the flat glass plates. For the fibroblasts growing on the glass balls with diameters of 300 μm and below, since the cell attachment rates of these balls were much lower than those of the balls with diameters of 500 μm and above, 35 cells in total were measured, and the results shown are for each individual cell.
Figure 18:
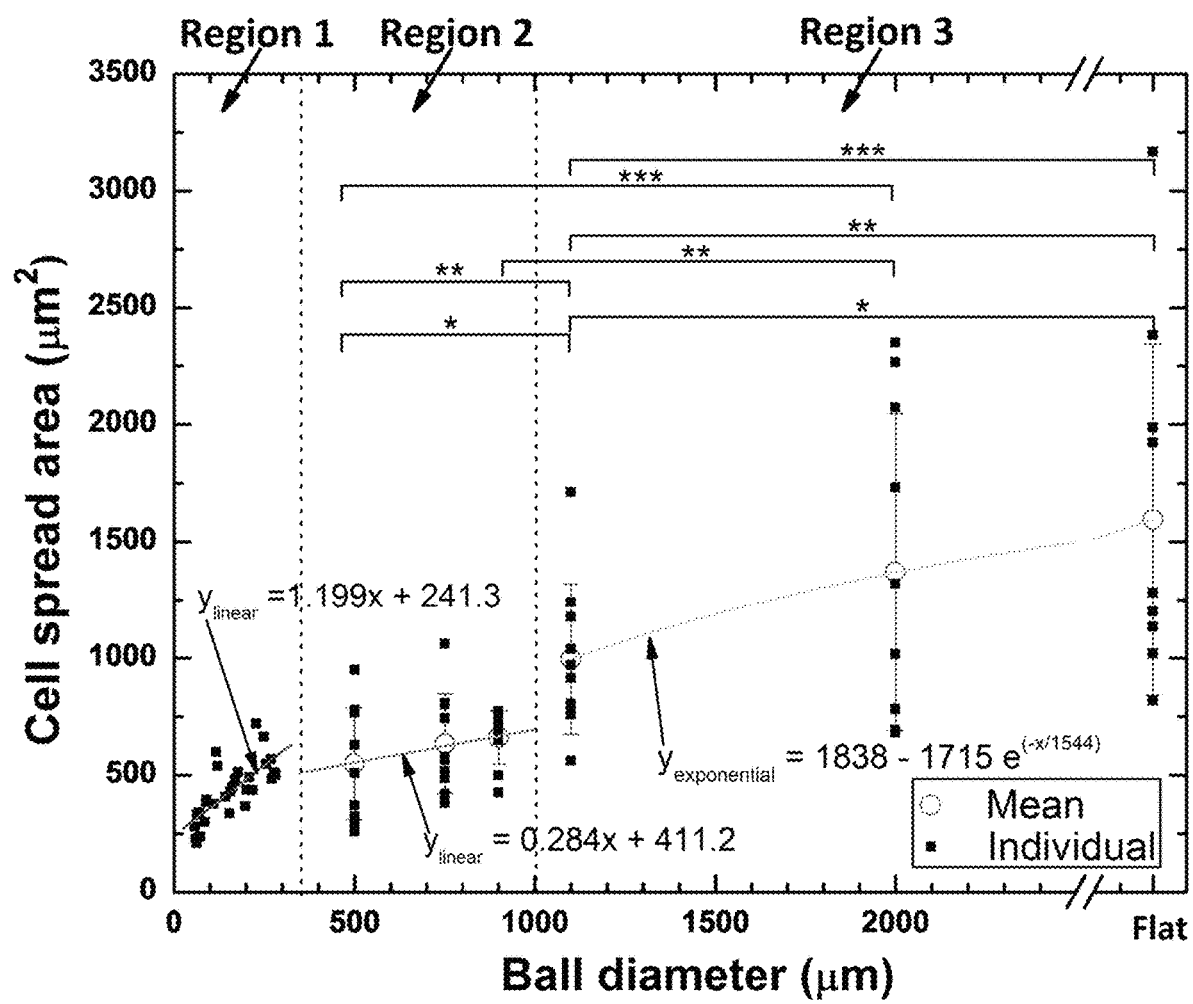
FIG. 18 shows cell spread area versus ball diameter for the NIH-3T3 fibroblasts measured in FIG. 17. In contrast to FIG. 17, here, for the fibroblasts growing on the glass balls with diameters of 500 μm and above, besides the mean±SD result for each ball diameter, the spread area of each individual fibroblast is also shown. *: $p<0.05$; : $p<0.01$; *: $p<0.001$.

FIG. 17 shows the measurement results of the cell dimensions of these measured fibroblasts. For the fibroblasts on the balls with diameters of 500 μm and above including the case of the flat plates (same in the below unless otherwise stated), the results shown are mean±SD for each ball diameter. For the fibroblasts on the balls with diameters of 300 μm and below, the results shown are for each individual cell. FIG. 18 shows the measurement results of the cell spread areas of these measured fibroblasts. The statistical analysis results of ANOVA with Tukey's post hoc test were added in FIG. 18. In contrast to FIG. 17, in FIG. 18, for the fibroblasts on the balls with diameters of 500 μm and above, besides the mean±SD result for each ball diameter, the spread area of each individual fibroblast is also shown. The measurement results and statistical analyses of these fibroblasts is shown in Table 1.

TABLE 1

Cell length, width, aspect ratio, and spread areas of NIH-3T3 fibroblasts grown on balls of various diameters.

| Ball diameter | | Flat | 2 mm | 1.1 mm | 900 μm |
|---|---|---|---|---|---|
| Cell length (μm) | mean ± SD | 110.1 ± 26.9 | 112.9 ± 40.7 | 117.8 ± 48.0 | 78.8 ± 14.3 |
| | maximum | 177.1 | 197.4 | 230.8 | 98.3 |
| | minimum | 84.6 | 64.8 | 64.0 | 54.5 |
| Cell width (μm) | mean ± SD | 25.2 ± 23.4 | 25.5 ± 10.6 | 17.0 ± 2.7 | 16.0 ± 2.3 |
| | maximum | 86.7 | 47.7 | 20.8 | 19.2 |
| | minimum | 13.5 | 15.5 | 13.4 | 12.8 |
| Cell aspect ratio | mean ± SD | 0.248 ± 0.245 | 0.275 ± 0.204 | 0.165 ± 0.072 | 0.213 ± 0.069 |
| | maximum | 0.879 | 0.717 | 0.326 | 0.337 |
| | minimum | 0.062 | 0.105 | 0.098 | 0.133 |
| Cell spread Area (μm²) | mean ± SD | 1592.3 ± 751.9 | 1368.4 ± 678.1 | 996.7 ± 322.0 | 660.1 ± 113.4 |
| | maximum | 3166.7 | 2347.3 | 1710.1 | 771.1 |
| | minimum | 816.2 | 679.9 | 559.7 | 424.2 |

| Ball diameter | | 750 μm | 500 μm | 300 μm and below |
|---|---|---|---|---|
| Cell length (μm) | mean ± SD | 76.0 ± 18.0 | 94.2 ± 44.5 | 59.1 ± 28.9 |
| | maximum | 105.4 | 164.5 | 116.8 (on a 249.5 μm-ball) |
| | minimum | 55.6 | 42.6 | 12.4 (on a 70.6 μm-ball) |
| Cell width (μm) | mean ± SD | 14.7 ± 2.9 | 16.1 ± 3.0 | 15.2 ± 2.9 |
| | maximum | 20.1 | 20.6 | 22.4 (on a 91.2 μm-ball) |
| | minimum | 11.3 | 12.5 | 10.0 (on a 74.1 μm-ball) |
| Cell aspect ratio | mean ± SD | 0.203 ± 0.061 | 0.208 ± 0.102 | 0.357 ± 0.250 |
| | maximum | 0.311 | 0.424 | 0.907 (on a 70.6 μm-ball) |
| | minimum | 0.121 | 0.089 | 0.130 (on a 249.5 μm-ball) |
| Cell spread Area (μm²) | mean ± SD | 634.5 ± 212.5 | 549.2 ± 238.4 | 429.0 ± 124.9 |
| | maximum | 1059.5 | 948.5 | 719.7 (on a 227.8 μm-ball) |
| | minimum | 379.6 | 257.5 | 208.7 (on a 63.0 μm-ball) |

In FIG. 17, for the cell lengths, the overall trend is, starting from the case of the flat plates, the mean length of the fibroblasts did not decrease significantly with the decrease of the substrate ball diameter down to 300 µm when the monotonic decrease of the cell length started. For the fibroblasts on the balls with diameters of 300 µm and below, in contrast to the lengths of the fibroblasts, the widths of the fibroblasts did not distribute widely.

For the fibroblasts on the 2 mm-balls and the fibroblasts on the flat plates, except for the large difference in the SD values of their cell widths, their mean cell widths were similar, which is supported by their similar well-spread cell morphologies with two or three lamellipodia as shown in FIGS. 16 (a) and (b). With the decrease of the ball diameter from 2 mm to 1.1 mm, both the mean cell width and the corresponding SD value decreased abruptly, which also agreed with the significant changes in the cell morphology (FIGS. 16 (b) and (c)). For all the fibroblasts on the balls with diameters of 1.1 mm and below, the cell widths were similar and did not vary significantly, i.e., there was no significant further decrease in the cell width with the decrease in the ball diameter, and the mean cell width of all these cells was 15.3 µm. Also, as shown in FIG. 16 (c-h), the spindle-shape was the dominant cell morphology of all these fibroblasts. Since the cell nucleus must be enclosed in the cell body, the minimum width of a spindle-shaped cell is decided by the minimum width of the cell nucleus, which explains why the cell widths of all the fibroblasts on the balls with diameters of 1.1 mm and below were similar and provides a measurement for the minimum width of the cell nucleus of an attached and spread cell.

The dramatically-wide distribution of the cell aspect ratios of the fibroblasts on the balls with diameters of 300 µm and below (FIG. 17) is due to the morphology, round shape with one or two long and narrow lamellipodia, of some of these fibroblasts.

In FIG. 18, for the fibroblasts on the balls with diameters of 500 µm and above, the mean cell spread area decreased monotonically with the decrease of the ball diameter, from the flat plates to the larger balls to the smaller balls, and decreased from 1592.3 µm$^2$ to 549.2 µm$^2$. The overall trend of the cell spread areas of the fibroblasts on the balls with diameters of 300 µm and below is a monotonic decrease with the decrease of the ball diameter, which is consistent with the overall trends of the measurement results of the cell dimensions of these fibroblasts, a monotonic decrease in the cell length and an insignificant variation in the cell width (FIG. 17).

As labeled in FIG. 18, according to the variation of the measured spread areas of the fibroblasts on the balls with diameters of 300 µm and below and the mean spread areas of the fibroblasts on the balls with diameters of 500 µm and above versus the ball diameter, all the measured cell spread areas were divided into the following three regions, Region 1, Region 2, and Region 3 (Lee and Yang, 2012). Region 1 includes the spread areas of the fibroblasts on the balls with diameters of 300 µm and below and these cell spread areas were fitted by a linear relation, $y_{linear}=1.199x+241.3$. Region 2 includes the spread areas of the fibroblasts on the balls with diameters of 500 µm, 750 µm, and 900 µm, and the corresponding three mean spread areas were fitted also by a linear relation, $y_{linear}=0.284x+411.2$. The slope of this linear relation was 23.7% of the slope of the fitting linear relation of Region 1. Region 3 includes the spread areas of the fibroblasts on the balls with diameters of 1.1 mm and 2 mm and on the flat plates, and the corresponding three mean spread areas were fitted by an exponential relation, $y_{exponential}=1838-1715e^{(-x/1544)}$. Because the radius of curvature of the flat plates is infinity, while the diameters of 1.1 mm and 2 mm are finite numbers, an exponential relation is the suitable relation to curve-fit the asymptotic trend of the mean spread areas of the fibroblasts on the balls with diameters from 1.1 mm to 2 mm to infinity (which is the case of the flat plates). The slope between the two data points of the mean spread areas for the fibroblasts on 1.1 mm- and 2 mm-balls was 0.413, which was 34.4% of the slope of the fitting linear relation of Region 1. Therefore, Region 1's fitting linear relation had the largest slope compared with those of Regions 2 and 3. Also, note that, from the 900 µm-balls to the 1.1 mm-balls, there was a 51.0% sudden rise in the mean cell spread area of the fibroblasts. From the above linear fitting analysis, we concluded that, overall, the cell spread area of the fibroblasts increased with the increase of the ball diameter with three different slopes in the three distinct regions depending on the ball diameters.

Example 7

Effects of the Substrate Curvatures on the Spreading Morphologies of the hMSCs

The surface curvature of a substrate is the reciprocal of the radius of the substrate.

We defined the cell attachment rate as the ratio between the number of the attached and spread cells on the glass balls and the number of the seeded cells in a cell culture dish. We did not quantitatively measure the cell attachment rates in this study, and the cell attachment rates were difficult to measure because the number of the attached and spread cells on the glass balls was difficult to count. As shown in FIGS. 15 (b) and (c), the embedded glass balls were packed on the surfaces of the PA gels. Since we seeded the same number of cells into each cell culture dish, we used the chance of finding an attached and spread cell on a glass ball as a qualitative measure of the cell attachment rate on the glass balls with a same diameter and packed on the surface of a PA gel.

Among the used diameters of glass balls, we found that the minimum diameter of a glass ball on which an hMSC can attach and spread was 500 µm. We qualitatively found that the cell attachment rate of the hMSCs decreased with the decrease of the substrate ball diameter.

Figure 19:
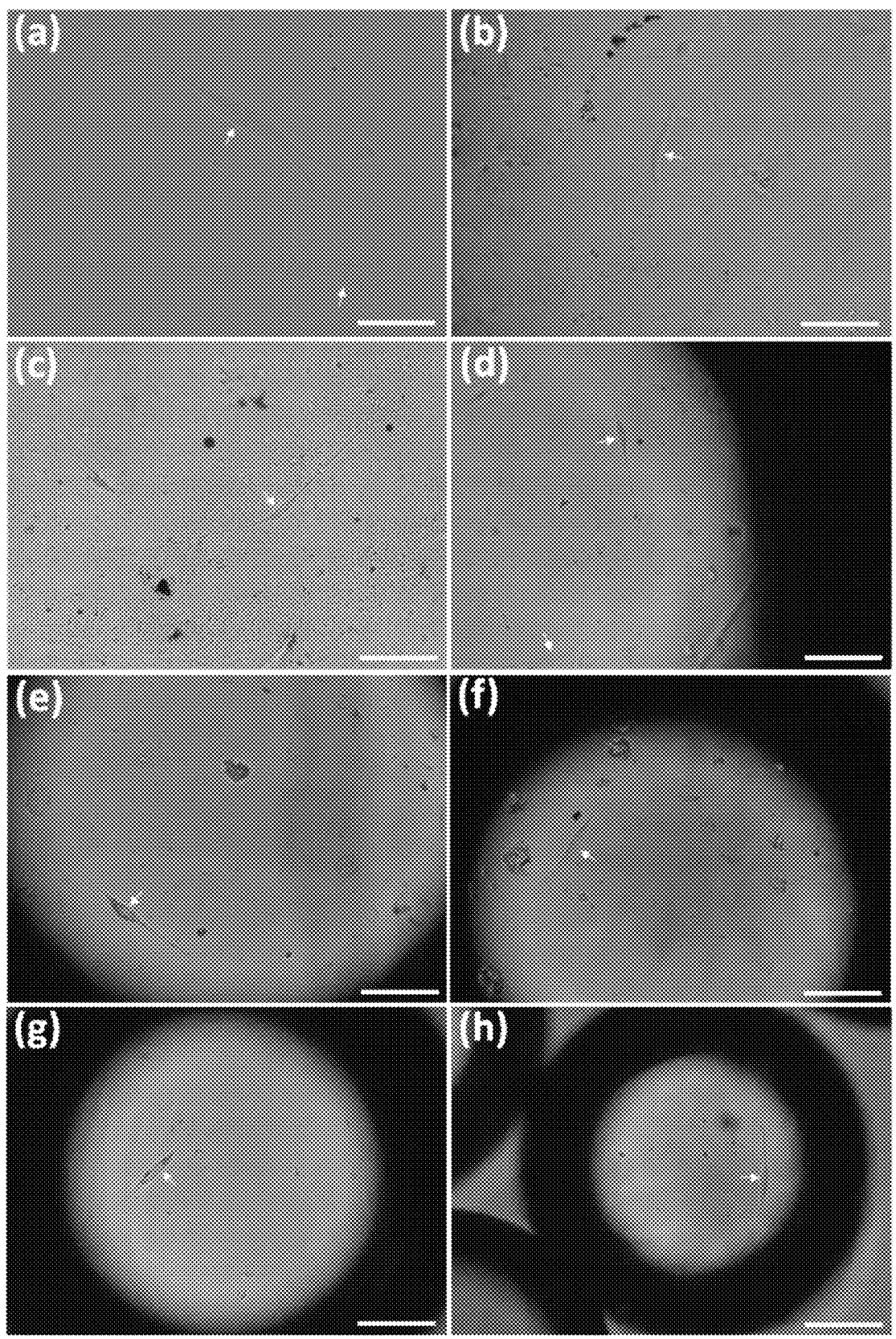
FIG. 19 shows effects of the substrate curvatures on the spreading morphologies of the normal human adipose-derived mesenchymal stem cells (hMSCs). The hMSCs were plated on the PA gels embedded with micro glass balls having diameters from 5 µm to 4 mm, and the phase-contrast images were taken after 96 h in culture (since the hMSCs spread much slower than the NIH-3T3 fibroblasts, the spreading morphologies of the hMSCs were imaged after 96 hours in culture, instead of the NIH-3T3 fibroblasts' imaging time, after 24 h in culture). hMSCs growing on a flat glass plate (a), and on a 4 mm-(b), 3 mm-(c), 2 mm-(d), 1.1 mm-(e), 900 nm-(f), 750 µm-(g), and 500 µm-(h) diameter glass ball are indicated by the white arrows. Scale bars: 100 µm.

FIG. 19 shows the effects of the substrate curvatures on the spreading morphologies of the hMSCs growing on the glass balls with various diameters. Since the hMSCs spread much slower than the NIH-3T3 fibroblasts, the spreading morphologies of the hMSCs were imaged after 96 hours in culture when the hMSCs started to divide, instead of the NIH-3T3 fibroblasts' imaging time, after 24 hours in culture (when the fibroblasts started to divide), which we used before (Lee and Yang, 2012).

In the following, for brevity, the words "growing", "glass", and "diameter" will be omitted unless this omission may induce unclarity. For examples, "hMSCs growing on the flat glass plate" will read as "hMSCs on the flat plate" and "hMSCs growing on the 2 mm-diameter glass ball" will read as "hMSCs on the 2 mm-ball".

After 96 hours in culture, the hMSCs on the flat plates were well-spread (FIG. 19 (a)), the hMSCs had at least two or three long or short narrow or wide lamellipodia, some of the hMSCs had five or more lamellipodia for active migration, some of the hMSCs were connected to each other by long lamellipodia and cell division began to occur at this time. In contrast to the hMSCs on the flat plates, the hMSCs on the 4 mm-, 3 mm-, 2 mm-, 1.1 mm-, 900 μm-, 750 μm-, and 500 μm-balls were much less spread, and regardless of the ball diameters, the majority of hMSCs on the balls had the same morphology, spindle-shape with two long or short narrow lamellipodia (FIG. 19 (b)-(h)). For each ball diameter including the case of the flat plates (same in the below unless otherwise stated), 30 randomly-selected hMSCs were observed and measured. Table 2 shows the total count of the hMSCs having the number of lamellipodia for each ball diameter. For the 30 hMSCs on the flat plates, the number of lamellipodia of each cell was random. Among the observed numbers of lamellipodia that an hMSC could have, three lamellipodia was the number of lamelipodia that had the maximum number of cells, which was 11. There were seven cells each of which had only two lamellipodia, which was the minimum number of lamellipodia observed in this study for an hMSC on a flat plate or a ball. There were two cells each of which had seven lamellipodia, which was the maximum number of lamellipodia observed in this study for an hMSC on a flat plate or a ball. For the 30 hMSCs on the balls with each of the diameters, there were only a small portion, from 2/30 (≈6.7%) to 7/30 (≈23.3%), of the cells having more than two lamellipodia. For all the 180 hMSCs on the balls having diameters of 3 mm and below, there were no any cells having more than three lamellipodia. For the 30 hMSCs on the 4 mm-balls, there was only one cell having four lamellipodia, and there were not any cells having more than four lamellipodia.

The fact that, no hMSCs were found to attach and spread on the balls with diameters of 300 μm and below, indicates that it is difficult for an hMSC to adhere to the surfaces of glass balls with small radii or large curvatures, such as the radii at or below 150 μm.

Example 8

Cell Dimensions of the Measured hMSCs

Figure 20:
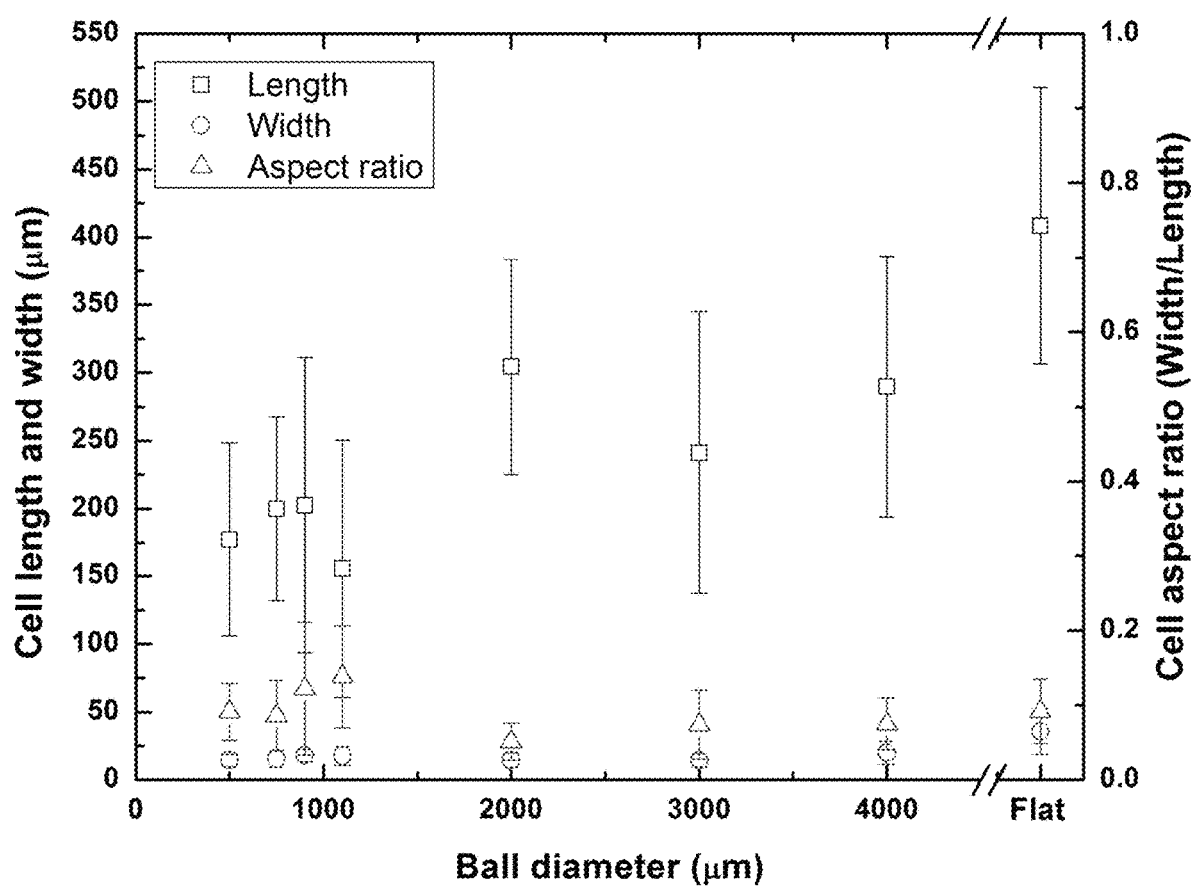
FIG. 20 shows cell length and width versus ball diameter for the hMSCs. The cell lengths and widths were measured for a number of randomly-selected cells ($n_{hmMSCs}$=240) growing on the flat glass plates and on the 4 mm-, 3 mm-, 2 mm-, 1.1 mm-, 950 µm-, 750 µm-, and 500 µm-glass balls. 30 cells were measured for each ball diameter including the case of the flat glass plates, and the results shown are mean±SD.
Figure 21:
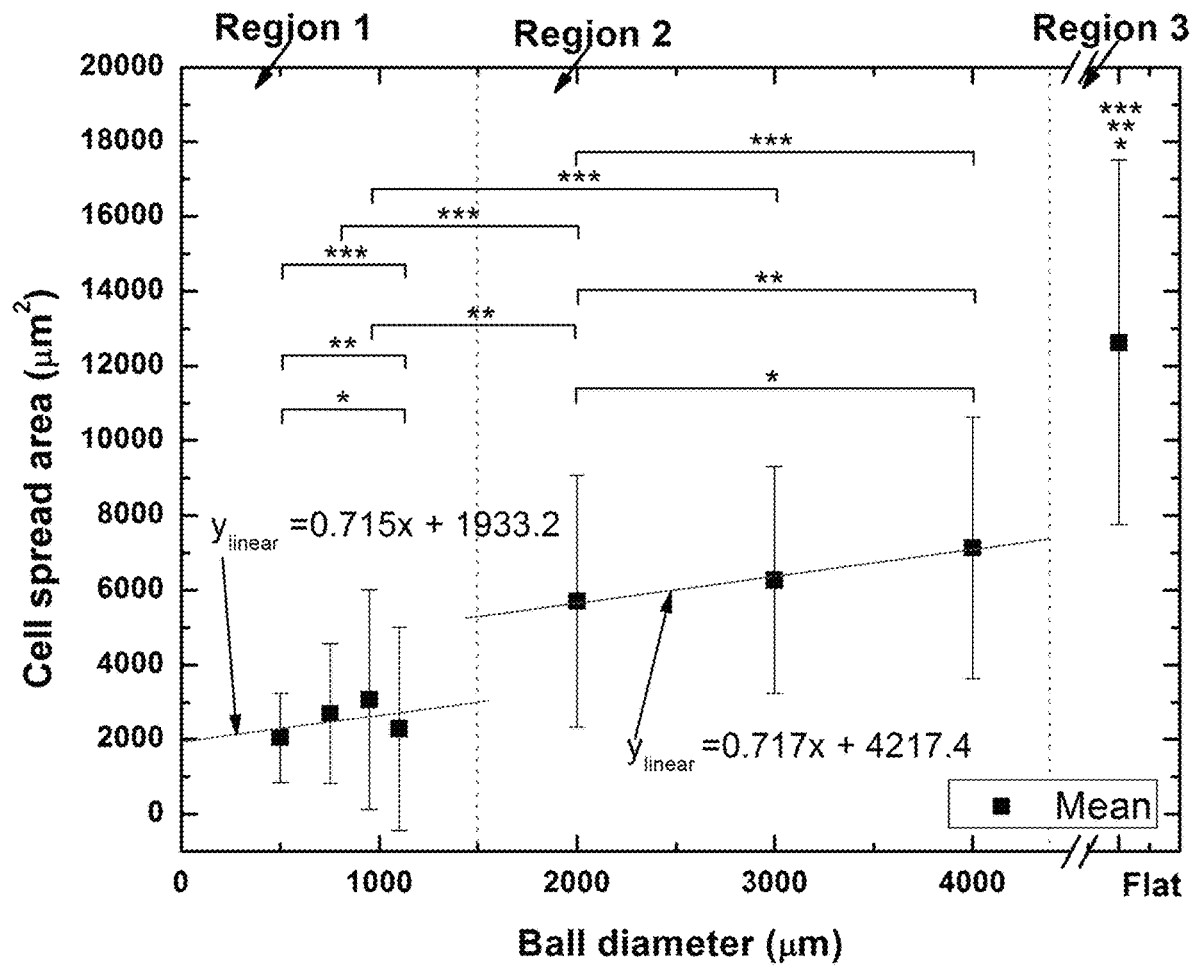
FIG. 21 shows cell spread area versus ball diameter for the hMSCs measured in FIG. 20. The results shown are mean±SD. *: $p<0.05$; : $p<0.01$; *: $p<0.001$.

For the cells growing on the balls, the cell dimensions, including the cell lengths and widths, and the cell spread areas are all important quantitative information to reveal the effects of the substrate curvatures on cell shape and function. The cell lengths and widths, and the cell spread areas were measured for the above-mentioned randomly-selected 30 hMSCs on the flat plates and 30 hMSCs for each of the above-mentioned seven ball diameters. FIG. 20 shows the measurement results of the cell dimensions of these measured hMSCs. FIG. 21 shows the measurement results of the cell spread areas of these measured hMSCs. Supplementary to FIGS. 20 and 21, Table 3 also lists the numerical results of the statistical analysis on these measurement results. In FIG. 20, overall the mean cell length of the hMSCs decreased monotonically with the decrease of the substrate ball diameter, and the mean cell length varied between 155.5 μm and 408.4 μm. According to the values of the mean cell lengths of the hMSCs, the mean cell lengths of the hMSCs can be divided into the following three groups. Group 1 includes the four mean cell lengths for the hMSCs on the 500 μm-, 750 μm-, 900 μm-, and 1.1 mm-balls, and these four mean cell lengths overall also have the similar values. Group 2 includes the three mean cell lengths for the hMSCs on the 2 mm-, 3 mm-, and 4 mm-balls, and these three mean cell lengths overall have the similar values. Group 3 includes only the mean cell length of the hMSCs on the flat plates. The mean cell lengths of the hMSCs on the 4 mm- and 2 mm-balls was 71.0% and 74.5% of that of the hMSCs on the flat plates, respectively, whereas the mean cell length of the NIH-3T3 fibroblasts on the 2 mm-balls was very similar to that of the fibroblasts on the flat plates (Lee and Yang, 2012). This observation indicates that the cell lengths of the hMSCs were much more sensitive than those of the fibroblasts to the

TABLE 2

Number of the hMSCs having the number of lamellipodia. The total number of the hMSCs measured for each ball diameter was 30. The "Mean ± SD" is the mean ± SD of the numbers of lamellipodia of the hMSCs growing on the balls of each diameter.

| Number of lamellipodia | Number of the hMSCs, growing on the balls of each diameter, having the number of lamellipodia | | | | | | | |
|---|---|---|---|---|---|---|---|---|
| | Flat | 4 mm | 3 mm | 2 mm | 1.1 mm | 900 μm | 750 μm | 500 μm |
| 1 | 0 | 0 | 0 | 0 | 0 | 0 | 0 | 0 |
| 2 | 7 | 23 | 24 | 24 | 27 | 28 | 26 | 26 |
| 3 | 11 | 6 | 6 | 6 | 3 | 2 | 4 | 4 |
| 4 | 8 | 1 | 0 | 0 | 0 | 0 | 0 | 0 |
| 5 | 2 | 0 | 0 | 0 | 0 | 0 | 0 | 0 |
| 6 | 0 | 0 | 0 | 0 | 0 | 0 | 0 | 0 |
| 7 | 2 | 0 | 0 | 0 | 0 | 0 | 0 | 0 |
| Mean ± SD | 3.4 ± 1.3 | 2.3 ± 0.5 | 2.2 ± 0.4 | 2.2 ± 0.4 | 2.1 ± 0.3 | 2.1 ± 0.3 | 2.1 ± 0.3 | 2.1 ± 0.3 | small curvatures or the large radii of the large substrate glass balls, e.g., the radii of 2 mm and 1 mm used here.

TABLE 3

Cell length, width, aspect ratio, and spread areas of hMSCs grown on balls of various diameters.

| Ball diameter | | Flat | 4 mm | 3 mm | 2 mm |
|---|---|---|---|---|---|
| Cell length (μm) | mean ± SD | 408.4 ± 102.1 | 289.8 ± 96.1 | 241.1 ± 103.9 | 304.4 ± 79.3 |
| | maximum | 622.1 | 584.6 | 478.2 | 512.4 |
| | minimum | 176.2 | 167.7 | 92.8 | 149.4 |
| Cell width (μm) | mean ± SD | 35.8 ± 16.9 | 20.1 ± 8.5 | 14.3 ± 4.8 | 14.5 ± 5.3 |
| | maximum | 85.2 | 44.0 | 29.5 | 38.0 |
| | minimum | 16.8 | 10.2 | 9.0 | 9.1 |
| Cell aspect ratio | mean ± SD | 0.092 ± 0.043 | 0.075 ± 0.035 | 0.074 ± 0.046 | 0.051 ± 0.025 |
| | maximum | 0.181 | 0.163 | 0.205 | 0.157 |
| | minimum | 0.027 | 0.026 | 0.025 | 0.025 |
| Cell spread Area (μm$^2$) | mean ± SD | 12629.2 ± 4883.7 | 7133.7 ± 3503.4 | 6269.3 ± 3024.7 | 5700.2 ± 3373.9 |
| | maximum | 22430.4 | 16336.6 | 13296.3 | 17798.6 |
| | minimum | 3790.0 | 2478.6 | 1683.6 | 1322.7 |

| Ball diameter | | 1.1 mm | 900 μm | 750 μm | 500 μm |
|---|---|---|---|---|---|
| Cell length (μm) | mean ± SD | 155.5 ± 94.8 | 202.4 ± 108.7 | 199.8 ± 67.8 | 177.2 ± 71.2 |
| | maximum | 527.5 | 506.0 | 389.7 | 341.2 |
| | minimum | 50.1 | 60.3 | 101.2 | 77.0 |
| Cell width (μm) | mean ± SD | 17.7 ± 7.0 | 18.0 ± 4.5 | 15.4 ± 6.0 | 14.5 ± 4.4 |
| | maximum | 35.5 | 27.4 | 42.0 | 24.7 |
| | minimum | 9.6 | 10.0 | 8.6 | 6.8 |
| Cell aspect ratio | mean ± SD | 0.138 ± 0.068 | 0.122 ± 0.089 | 0.086 ± 0.047 | 0.091 ± 0.038 |
| | maximum | 0.286 | 0.370 | 0.292 | 0.196 |
| | minimum | 0.037 | 0.041 | 0.043 | 0.039 |
| Cell spread Area (μm$^2$) | mean ± SD | 2282.8 ± 2725.6 | 3068.6 ± 2939.2 | 2698.2 ± 1879.1 | 2043.5 ± 1204.3 |
| | maximum | 13426.9 | 13220.4 | 8642.3 | 5794.8 |
| | minimum | 463.3 | 354.2 | 796.4 | 721.1 |

Except the mean cell width of the hMSCs on the flat plates, the mean cell widths of the hMSCs on all the balls (with diameters from 500 μm to 4 mm) were similar (FIG. 20), and the mean cell width of all the hMSCs on the balls with diameters from 500 μm to 4 mm was 16.4 μm. This similarity phenomenon observed here for all the mean cell widths of the hMSCs on the balls can be explained by the same spindle-shape cell morphology enclosing the cell nucleus, because the minimum width of a spindle-shaped cell is decided by the minimum width of the cell nucleus (FIG. 19 (b)-(h)). The mean cell width of the hMSCs on the flat plates increased abruptly from 20.1 μm, the mean cell width of the hMSCs on the 4 mm-balls, to 35.8 μm. This is consistent with the abrupt morphology change of most of the hMSCs, from the spindle-shape with two long or short narrow lamellipodia on the 4 mm-balls to the well-spread shape with randomly-multiple lamellipodia on the flat plates. The mean cell widths of the hMSCs on the 4 mm- and 2 mm-balls were 56.1% and 40.5% of that of the hMSCs on the flat plates, respectively, whereas the mean cell width of the NIH-3T3 fibroblasts on the 2 mm-balls was very similar to that of the fibroblasts on the flat plates (Lee and Yang, 2012). This observation indicates that the cell widths of the hMSCs were also much more sensitive than those of the fibroblasts to the small curvatures or the large radii of the large substrate glass balls, e.g., the radii of 2 mm and 1 mm used here.

The mean cell aspect ratio of these hMSCs varied between 0.051 and 0.138, which were much lower than those of the NIH-3T3 fibroblasts. The much lower mean cell aspect ratios of these hMSCs are due to the morphologies of most of these hMSCs, the spindle-shapes with two long or short lamellipodia (FIG. 19), whereas the morphologies of the fibroblasts were much more spread (Lee and Yang, 2012).

In FIG. 21, overall, similar to the case of the NIH-3T3 fibroblasts (Lee and Yang, 2012), the mean cell spread area of these hMSCs decreased with the decrease of the ball diameter, from the flat plates to the larger balls to the smaller balls. All the mean cell spread areas were divided into the following three regions, Region 1, Region 2, and Region 3 (FIG. 21), and the division of these three regions was the same to the division of the three groups of the mean cell lengths of these hMSCs in the above, i.e., the corresponding groupings of the ball diameters were the same. Region 1 includes the four mean cell spread areas of the hMSCs on the balls with diameters of 500 μm, 750 μm, 900 μm, and 1.1 mm, and these four mean cell spread areas were fitted by a linear relation, $y_{linear}=0.715x+1933.2$. Region 2 includes the three mean cell spread areas of the hMSCs on the balls with diameters of 2 mm, 3 mm, and 4 mm, and these three mean cell spread areas were fitted by another linear relation $y_{linear}=0.717x+4217.4$. Note that the slope of Region 2's fitting linear relation was very similar to that of Region 1's fitting linear relation. Region 3 includes only the mean cell spread area of the hMSCs on the flat plates. The mean cell spread areas of the hMSCs on the 4 mm- and 2 mm-balls was 56.5% and 45.1% of that of the hMSCs on the flat plates, respectively, whereas the mean cell spread area of the NIH-3T3 fibroblasts on the 2 mm-balls was 86.0% of that of the fibroblasts on the flat plates (Lee and Yang, 2012). This observation indicates that the cell spread areas of the hMSCs were also much more sensitive than those of the fibroblasts to the small curvatures or the large radii of the large substrate glass balls, e.g., the radii of 2 mm and 1 mm used here. This is consistent with the above observations on the dependence of the hMSC morphology (FIG. 19) on substrate curvature, and on the dependences of the hMSC length and width (FIG. 20) on substrate curvature. Also, note that, from the 1.1 mm-balls to the 2 mm-balls, there was a 149.7% abrupt rise in the mean cell spread area of the hMSCs.

DISCUSSION

The curvature of the surface to which a cell adheres has profound effects on cell attachment, migration, differentiation (with regard to stem cells) and morphology. The observed cell spreading and differentiation responses to substrate curvatures create new directions/paradigms of research in the area of cell and tissue mechanobiology.

NIH-3T3 fibroblasts were cultured on the micro glass ball embedded PA gels with Young's moduli of 75 kPa, 10 kPa, and 1 kPa, respectively, and have showed that some cells could wrap over the balls and these cells naturally isotropically spread over the balls and the adjacent gel surfaces. The observations shown herein indicate that wrapping over a ball is a method to realize cell natural isotropic-spreading where the resulting cell outline or boundary is roughly circular and smooth which means the extent of the cell spreading in every direction is roughly the same from the geometric center of the cell. For a fibroblast wrapped over a ball, the inventors have reasonably estimated the spread area on the ball, the spread area on the gel surface, and the total spread area of this cell. Based on the measured projected area of this cell, the inventor estimated the diameter of this cell and compared this estimated value with the diameter of the micro glass ball to show the further spreading of this cell on the gel surface in the radial direction. Qualitative comparisons between the different fibroblasts, growing on the micro glass balls with different diameters and embedded in PA gels with different Young's moduli, for the above estimation results agreed well with the theoretical reasonings.

The cell natural isotropic-spreading observed herein shows a new paradigm for controlling the spreading of a cell and its applications in 3-D cellular bioengineering and mechanobiology. In the future, in combination with other imaging techniques, 3-D configurations of the embedded micro glass balls and the cells wrapping over the micro glass balls will be revealed. Micro glass ball embedded gels with controlled positions of the embedded balls and controlled emerging-out heights of these balls from the gel surfaces will be developed to systematically study the phenomena and the underlying mechanisms of the cell natural isotropic-spreading and to explore the wide applications of the observed cell natural isotropic-spreading in cellular bioengineering and mechanobiology.

Figure 22:
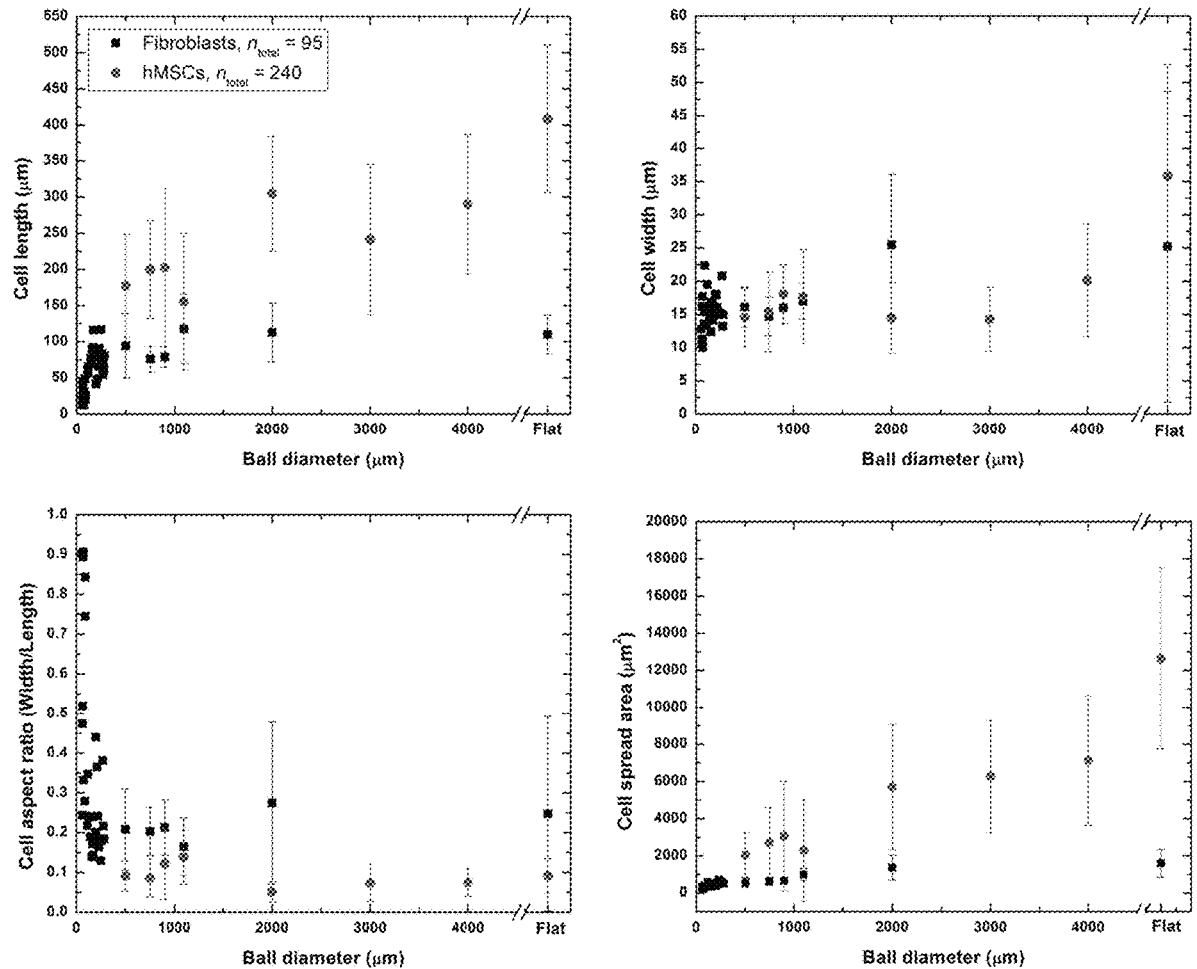
FIG. 22 shows the results for the cell lengths, cell widths, cell aspect ratios, and cell spread areas of both the NIH-3T3 fibroblasts ($n_{fibroblasts}$=95) and hMSCs ($n_{hmMSCs}$=240) plotted in FIG. 17 and FIG. 20, and FIG. 18 and FIG. 21 are re-plotted together as single plots for the cell length (a), cell width (b), cell aspect ratio (c), and cell spread area (d) versus the ball diameter, respectively.

The dimensions and spread areas of NIH-3T3 fibroblasts and hMSCs plated on the micro glass balls with diameters from 5 µm to 4 mm were observed and measured. The results of these two cell types were compared. For the convenience of the comparisons, FIG. 22 shows the measured results of both the fibroblasts and the hMSCs together as single plots for the cell lengths (FIG. 22 (a)), cell widths (FIG. 22 (b)), cell aspect ratios (FIG. 22 (c)), and cell spread areas (FIG. 22 (d)), respectively, i.e., FIG. 22 is the combination of FIG. 17 and FIG. 18, and FIG. 20 and FIG. 21. The similarity between the responses of these two cell types to the substrate curvatures or the substrate ball diameters showed the following: the mean cell spread areas of both cell types on the glass balls decreased with the decrease of the ball diameter.

The differences between the responses of these two cell types to the substrate curvatures or the substrate ball diameters included the following conclusions of the comparisons between their responses. Among the used diameters of glass balls, the minimum diameter of a ball on which an hMSC can attach and spread was 500 µm, whereas the minimum diameter of a ball on which an NIH-3T3 fibroblast can attach and spread without wrapping over the ball was 58 µm (A fibroblast wrapping over a ball means this fibroblast covered the entire upper exposed portion of the embedded ball in a PA gel and further spread on the adjacent gel surface) (Lee and Yang, 2012). This finding shows that the attachments of the hMSCs were much more sensitive to the large curvatures or the small radii of the small substrate glass balls than those of the fibroblasts.

Below 500 µm, the next ball diameter that we used in the Examples presented was 300 µm, and as stated in the Experiments above, no hMSCs attached and spread on the balls with diameters of 300 µm and below. From Table 3, the mean cell length of the hMSCs on the flat plates was 408.4 µm. The spreading morphologies were observed and the dimensions and spread areas were measured for hMSCs plated on the glass balls with diameters from 500 µm to 4 mm and on the flat glass plates. While the spreading morphologies of the fibroblasts on the 2 mm-balls were almost indistinguishable from those of the fibroblasts on the flat plates, the hMSCs here on the 4 mm-balls were majorly spindle-shaped with only two lamellipodia, but the hMSCs on the flat plates were well-spread with randomly-multiple lamellipodia. With the consideration that the surface of a 4 mm-ball is virtually flat with respect to the size of an hMSC, this finding indicates that the spreading morphologies of the hMSCs were much more sensitive to the small curvatures or the large radii of the large substrate glass balls than those of the fibroblasts. Putting this together with the relevant observations on the cell lengths, widths, and spread areas, described in the Examples herein, we say that the spreading morphologies, lengths, widths, and spread areas of the hMSCs were all much more sensitive to the small curvatures than those of the fibroblasts.

On the balls with diameters from 500 µm to 2 mm, the morphologies of the fibroblasts varied from the well-spread shapes on the 2 mm-balls to the round-shapes on the 500 µm-balls (Lee and Yang, 2012), whereas the morphologies of the hMSCs here on the balls with diameters from 500 µm to 4 mm were always majorly spindle-shaped with only two lamellipodia. This finding shows that the spreading morphologies of the fibroblasts were much more sensitive to the intermediate curvatures or the radii of the intermediate-sized substrate glass balls than those of the hMSCs.

Overall, starting from the case of the flat plates, the mean cell length of the hMSCs decreased monotonically with the decrease of the substrate ball diameter. The values of the mean cell lengths of the hMSCs were divided into the three groups, and the corresponding grouping of the ball diameters was same to that for the mean cell spread areas of these hMSCs, which may be understood by the observed similar mean cell widths of the hMSCs on the balls with different diameters. The mean±SD results of all the cell lengths, all the cell widths, and all the cell aspect ratios of the hMSCs on the balls with diameters of 500 µm and above, including the case of the flat plates, were 247.3±90.5 µm, 18.8±7.2 µm, and 0.091±0.049, respectively.

To study the underlying biophysical mechanisms for the observed effects of the substrate curvatures on the spreading of the hMSCs, how the observed spreading morphologies (FIG. 19) and measured sizes (FIGS. 20 and 21) of the hMSCs can be scaled with the diameters of the substrate ball was also investigated. In conclusion, the hMSCs have been cultured on the micro glass ball embedded PA gels, prepared with an improved protocol, and the glass balls had diameters from 5 µm to 4 mm. The spreading morphologies of the hMSCs growing on the balls were observed, and it was found that the hMSCs on the balls were almost uniformly spindle-shaped with two lamellipodia. The cell dimensions and spread areas of these hMSCs were also measured, and the mean cell spread area showed a decreasing tendency with the decreasing of the substrate ball diameter. The obtained results here for the hMSCs were compared with those for the NIH-3T3 fibroblasts. The attachments of the hMSCs were much more sensitive to the large curvatures of the small balls than those of the fibroblasts. The spreading morphologies of the hMSCs were much more sensitive to the small curvatures of the large balls than those of the fibroblasts. But the spreading morphologies of the fibroblasts were much more sensitive to the intermediate curvatures of the intermediate-sized balls than those of the hMSCs. Therefore, substrate curvature directs cell attachment and spreading, and a larger substrate curvature means less cell attachment and spreading, and a smaller substrate curvature means more cell attachment and spreading. This substrate curvature effect is different for different cell types. All these show that the curvature of a substrate is an important geometric parameter that can be utilized and tuned for cell and tissue engineering, and the idea of the micro glass ball embedded gels used here provides a paradigm for this purpose. Thus, substrate curvatures affect cell behaviors/functions, including cell adhesion, spreading, migration, division, differentiation, apoptosis, signal transduction, communication, etc.

All patents, patent applications, provisional applications, and publications referred to or cited herein are incorporated by reference in their entirety, including all figures and tables, to the extent they are not inconsistent with the explicit teachings of this specification. By citation of various references in this document, the Applicant does not admit any particular reference is "prior art" to their invention.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the disclosure without limitation thereto.

REFERENCES

Alberts, B., A. Johnson, J. Lewis, D. Morgan, M. Raff, K. Roberts, and P. Walter (2015) *Molecular Biology of the Cell*. Garland Science, N.Y., USA, sixth edition.

Alenghat F J, Ingber D E (2002) Mechanotransduction: all signals point to cytoskeleton, matrix, and integrins. *Sci STKE*. 119, PE6.

American Type Culture Collection (ATCC, http://atcc.org/), Manassas, Va., USA.

Baker B M, Chen C S (2012) Deconstructing the third dimension—how 3D culture microenvironments alter cellular cues. *J Cell Sci*. 125(13), 3015-3024.

Beltran S, Baker J P, Hooper H H, Blanch H W, Prausnitz J M (1991) Swelling equilibria for weakly ionizable, temperature-sensitive hydrogels. *Macromolecules*. 24(2), 549-551.

Brown X Q, Ookawa K, Wong J Y (2006) Evaluation of polydimethylsiloxane scaffolds with physiologically-relavant elastic moduli: interplay of substrate mechanics and surface chemistry effects on vascular smooth muscle cell response. *Biomaterials*. 26, 3123-3129.

Buxboim A, Rajagopal K, Brown A X, Discher D E (2010) How deeply cell feel: methods for thin gels. *J Phys: Condens Matter*. 22(19), 194116.

Chen C S, Tan J, Tien J (2004) Mechanotransduction at cell-matrix and cell-cell contracts. *Annu Rev Biomed Eng*. 6, 275-302.

Chen, C. S., M. Mrksich, S. Huang, G. M. Whitesides, and D. E. Ingber (1997) Geometric control of cell life and death. *Science*. 276:1425-1428.

Cheng C-M, Steward R L Jr, Leduc P R (2009) Probing cell structure by controlling the mechanical environment with cell-substrate interactions. *J Biomech*. 42, 187-192.

Dennis Discher (2006) "Matrix elasticity directs stem cells lineage specification", *Cell*, 126, 677-689.

Digabel J I, Ghibaudo M, Trichet L, Richert A, Ladoux B (2010) Microfabricated substrates as a tool to study cell mechanotransduction. *Med Biol Eng Compt*. 48(10), 965-976.

Discher, D. E., P. Janmey, and Y.-L. Wang (2005) Tissue cells feel and respond to the stiffness of their substrate. *Science*. 310:1139-1143.

Dunn, G. A., and J. P. Heath (1976) A new hypothesis of contact guidance in tissue cells. *Exp. Cell Res*. 101:1-14.

Engler A J, Griffin M A, Sen S, Bonnemann C G, Sweeney H L, Discher D E (2004) Myotubes differentiate optimally on substrates with tissue-like stiffness: pathological implications for soft or stiff microenvironments. *J Cell Biol*. 166(6), 877-887.

Engler, A. J., S. Sen, H. L. Sweeney, and D. E. Discher (2006). Matrix elasticity directs stem cell lineage specification. *Cell*. 126:677-689.

Folch A, Toner M (2000) Microengineering of cellular interaction. *Annu Rev Biomed Eng*. 2, 227-256.

Georges P C, Janmey P A (2005) Cell-type specific response to growth on soft material. *J Appl Physiol*. 98, 1547-1553.

Hirotsu S (1987) Phase transition of a polymer gel in pure and mixed solvent media. *J Phys Soc Jpn*. 56, 233-242.

Hwang, C. M., Y. Park, J. Y. Park, K. Lee, K. Sun, A. Khademhosseini, and S. H. Lee (2009) Controlled cellular orientation on PLGA microfibers with defined diameters. *Biomed Microdevices*. 11:7389-7397.

Janmey P A, Weitz D A (2004) Dealing with mechanics: mechanisms of force transduction. *Trends Biochem Sci*. 29(7), 364-370.

Kasza K E, Rowat A C, Liu J, Angelini T E, Brangwynne C P, Koenderink G H, Weitz D A (2007) The cell as a material. *Curr Opin Cell Biol*. 19, 101-107.

Kilian, K. A., B. Bugarija, B. T. Lahn, and M. Mrksich (2010) Geometric cues for directing the differentiation of mesenchymal stem cells. *Proc. Natl. Acad. Sci. USA* 107:4872-4877.

Kobayashi T, Sokabe M (2010) Sensing substrate rigidity by mechanosensitive ion channels with stress fibers and focal adhesions. *Curr Opini Cell Biol*. 22, 669-676.

Lee, S. J., and S. Yang (2012) Micro glass ball embedded gels to study cell mechanobiological responses to substrate curvatures. *Rev. Sci. Instr*. 83(9), e094302.

Life Technologies Corporation, Thermo Fisher Scientific Inc. (https://www.thermofisher.com/), Grand Island, N.Y., USA.

Liu, W. F., and C. S. Chen (2007) Cellular and multicellular form and function. *Advanced Drug Delivery Reviews*. 59:1319-1328.

Lo, C.-M., H.-B. Wang, M. Dembo, and Y.-L. Wang (2000) Cell movement is guided by the rigidit y of the substrate. *Biophysical Journal* 79:144-152.

Meehan S, Nain A S (2014) Role of suspended fiber structural stiffness and curvature on single-cell migration, nucleus shape, and focal-adhesion-cluster length. *Biophys J.* 107(11), 2604-2611.

Rape A D, Guo W-H, Wang Y L (2011) The regulation of traction force in relation to cell shape and focal adhesions. *Biomaterials.* 32, 2043-2051.

Rodriguez M L, McGarry P J, Sniadecki N J (2013) Review on cell mechanics: Experimental and modeling approaches. *Appl Mecha Rev.* 65, 60801.

Rumpler M, Woesz A, Dunlop J W C, van Dongen J T, Fratzl P (2008) The effect of geometry on three-dimensional tissue growth. *J R Soc Interface.* 5, 1173-1180.

Sanz-Herrera J A, Moreo P, Garcia-Aznar J M, Doblare M (2009) On the effect of substrate curvature on cell mechanics. *Biomaterials.* 30, 6674-6686.

Smeal R M, Rabbitt R, Biran R, Tresco P A (2005) Substrate curvature influences the direction of nerve outgrowth. *Annals Biomed Eng.* 33(3), 376-382.

Sniadecki N J, Desai R A, Ruiz S A, Chen C S (2006) Nanotechnology for cell-substrate interactions. *Annu Biomed Eng.* 34(1), 59-74.

Song, W., N. Kawazoe, and G. Chen (2011) Dependence of spreading and differentiation of mesenc hymal stem cells on micropatterned surface area. *Journal of Nanomaterials.* 2011:e265251.

Tanaka T, Nishio I, Sun S (1992) Crosslinked polyacrylamide, large volume change as a result of very small change in solvent, temperature, pressure. Patent: U.S. Pat. No. 5,100,933 A.

Tang, X., M. Y. Ali, and M. T. A. Saif (2012) A novel technique for micro-patterning proteins and cells on polyacrylamide gels. *Soft Matter.* 8:7197-7206.

Vartanian K B, Kirkpatrick S J, Hanson S R, Hinds M T (2008) Endotherial call cytoskeletal alignment independent of fluid shear stress on micropatterned surface. *Biochem Biophys Res Comm.* 371, 787-792.

Veiseh O, Doloff J C, Ma M, Vegas A J, Tam H H, Bader A R, Li J, Langan E, Wyckoff J, Loo W S, Jhunjhunwala S, Chiu A, Siebert S, Tang K, Hollister-Lock J, Aresta-Dasilva S, Bochenek M, Mendoza-Elias J, Wang Y, Qi M, Lavin D M, Chen M, Dholakia N, Thakrar R, Lacik I, Weir G C, Oberholzer J, Greiner D L, Langer R, Anderson D G (2015) Size- and shape-dependent foreign body immune response to materials implanted in rodents and non-human primates. *Nat Mater.* 14, 643-51.

Viswanathan P, Ondeck M G, Chirasatitsin S, Ngamkham K, Reilly G C, Engler A J, Battaglia G (2015) 3D surface topology guides stem cell adhesion and differentiation. *Biomaterials.* 52, 140-147.

Vogel V, Sheetz M (2006) Local force and geometry sensing regulate cell functions. *Nat Rev Mol Cell Biol.* 7, 265-275.

Wan, L. Q., S. M. Kang, G. Eng, W. L. Grayson, X. L. Lu, B. Huo, J. Gimble, X. E. Guo, V. C. Mow, and G. Vunjak-Novakovic (2010) Geometric control of human stem cell morphology and differentiation. *Integr. Biol.* 2:346-353.

Wang N, Tolic-Norrelykke I M, Chen J, Mijailovich S M, Butler J P, Fredberg J J, Stramenovic D (2002) Cell Stress. I. Stiffness and prestress are closely associated in adherent contractile cells. *Am J Physio Cell Physiol.* 282, c606-c616.

Wang, Y. L., and R. J. Pelham Jr. (1998) Preparation of a flexible, porous polyacrylamide substrate for mechanical studies of cultured cell. *Methods in Enzym.* 298:489-496.

Wong J Y, Leach J B, Brown X Q (2004) Balance of chemistry, topography, and mechanics at the cell-biomaterial interface: Issues and challenges for assessing the role of substrate mechanics on cell response. *Surf Sci.* 570, 119-133.

Yao, X., Peng, R., and Ding, J. (2013) Effects of aspect ratios of stem cells on lineage commitments with and without induction media. *Biomaterials.* 34:930-939.

Yeung T, Georges P C, Flanagan L A, Marg B, Ortiz M, Funaki M, Zahir N, Ming W, Weaver V M, Janmey P A (2004) Effects of substrate stiffness on cell morphology, cytoskeletal structure, and adhesion. *Cell Motil Cyto.* 60, 24-34.

Zadpoor A A (2015) Bone tissue regeneration: the role of scaffold geometry. *Biomat Sci.* 3(2), 231-245.

What is claimed is:

1. A method to modulate the relative osteogenic gene expression of a mesenchymal stem cell in the presence of osteocyte differentiation induction media by culturing the mesenchymal stem cell on a ball having a diameter and choosing a diameter between 500 μm and 6 mm, excluding 3 mm, comprising: culturing the mesenchymal stem cell on a ball, comprising the chosen diameter between about 500 μm and about 6 mm excluding 3 mm, wherein the level of the relative osteogenic gene expression of the mesenchymal stem cell decreases as the diameter of the substrate ball increases from about 500 μm to about 3 mm, the level of the relative osteogenic gene expression of the mesenchymal stem cell increases as the diameter of the ball increases from about 3 mm to about 6 mm and the level of the relative osteogenic gene expression of the mesenchymal stem cell on a ball of a diameter about 3 mm is comparable to that of the mesenchymal stem cell on a flat plate.

2. The method of claim 1, wherein the ball comprises a coating selected from the group consisting of a cell adhesive, a cell adhesion-promotor, a cell repellent, or a combination thereof.

3. The method of claim 1, wherein the ball is a glass ball.

* * * * *